US007807616B2

(12) United States Patent
Meine et al.

(10) Patent No.: US 7,807,616 B2
(45) Date of Patent: Oct. 5, 2010

(54) GERANONITRILE SUBSTITUTE

(75) Inventors: Georg Meine, Mettmann (DE); Theo ten Pierik, Venlo (NL)

(73) Assignee: Henkel AG & Co. KGaA, Duesseldorf (DE)

( * ) Notice: Subject to any disclaimer, the term of this patent is extended or adjusted under 35 U.S.C. 154(b) by 393 days.

(21) Appl. No.: 11/747,116

(22) Filed: May 10, 2007

(65) Prior Publication Data

US 2007/0265183 A1 Nov. 15, 2007

Related U.S. Application Data

(63) Continuation of application No. PCT/EP2005/011072, filed on Oct. 14, 2005.

(30) Foreign Application Priority Data

Nov. 11, 2004 (DE) ....................... 10 2004 054 620

(51) Int. Cl.

| | |
|---|---|
| ***A61K 8/00*** | (2006.01) |
| ***A61K 8/18*** | (2006.01) |
| ***A61Q 13/00*** | (2006.01) |
| ***C11D 3/50*** | (2006.01) |
| ***C11D 9/44*** | (2006.01) |
| *C07C 255/00* | (2006.01) |
| *C07C 253/00* | (2006.01) |

(52) U.S. Cl. ............................... 512/1; 512/6; 510/101; 558/303; 558/388

(58) Field of Classification Search ..................... 512/6, 512/1; 510/101; 252/522; 558/388, 303; 239/53

See application file for complete search history.

(56) References Cited

U.S. PATENT DOCUMENTS

| | | | | |
|---|---|---|---|---|
| 3,158,615 | A | 11/1964 | Dunn et al. | |
| 3,215,719 | A | 11/1965 | Allen et al. | |
| 4,162,984 | A | 7/1979 | DeBlock | |
| 4,351,737 | A | 9/1982 | Billenstein | |
| 4,376,789 | A | 3/1983 | Lowicki et al. | |
| 4,524,009 | A | 6/1985 | Valenty | |
| 4,639,325 | A | 1/1987 | Valenty | |
| 4,816,553 | A | 3/1989 | Baur et al. | |
| 4,820,439 | A | 4/1989 | Rieck | |
| 4,985,553 | A | 1/1991 | Fuertes et al. | |
| 5,780,420 | A | 7/1995 | Scheibel | |
| 5,501,814 | A | 3/1996 | Engelskirchen et al. | |
| 5,541,316 | A | 7/1996 | Engelskirchen et al. | |
| 5,705,169 | A | 1/1998 | Stein | |
| 5,730,960 | A | 3/1998 | Stein | |
| 5,821,360 | A | 10/1998 | Engelskirchen et al. | |
| 5,922,670 | A | 7/1999 | Knuebel | |
| 5,959,101 | A | 9/1999 | Engelskirchen et al. | |
| 6,187,055 | B1 | 2/2001 | Kottwitz et al. | |
| 6,455,086 | B1 | 9/2002 | Trinh et al. | |
| 2002/0032147 | A1* | 3/2002 | Foley et al. | 512/25 |
| 2003/0024997 | A1* | 2/2003 | Welch et al. | 239/53 |
| 2003/0176313 | A1* | 9/2003 | Ellwood et al. | 512/8 |

FOREIGN PATENT DOCUMENTS

| | | |
|---|---|---|
| DE | 2822891 | 12/1978 |
| DE | 3808114 | 9/1989 |
| DE | 4014055 | 11/1991 |
| DE | 4321022 | 1/1995 |
| DE | 4400024 | 7/1996 |
| DE | 1961063 | 9/1996 |
| DE | 19513391 | 10/1996 |
| DE | 19600018 | 7/1997 |
| DE | 19712033 | 9/1998 |
| EP | 0013780 | 8/1980 |
| EP | 043547 | 1/1982 |
| EP | 0046970 | 3/1982 |
| EP | 0150930 | 8/1985 |
| EP | 0164514 | 12/1985 |
| EP | 0232202 | 8/1987 |
| EP | 0280223 | 8/1988 |
| EP | 0427349 | 5/1991 |
| EP | 0542496 | 5/1993 |
| EP | 0693471 | 1/1996 |
| EP | 0694521 | 1/1996 |
| EP | 0472042 | 2/1996 |
| EP | 698140 | 2/1996 |
| EP | 0703292 | 3/1996 |
| EP | 0728749 | 8/1996 |
| EP | 0816291 | 1/1998 |
| EP | 0818450 | 1/1998 |
| GB | 2199855 | 7/1988 |
| GB | 2202244 | 9/1988 |

(Continued)

OTHER PUBLICATIONS

Cintronellyl nitrile product literature The Good Scents Company {www.thegoodscentscompany.com/data/rw1008931}.*

K. Schulze, Fettalkohoxäthylatacetate, Seifen-Öle Fette, Waschse 101, 37 (1975) pp. 37-44.

E. Stroink, "Eigenschaften und Anwendungsmöglichkeiten von Ethercarbonsäuren in Wasch-und Reinigungsmittein", Seifen-Öle Fette, Waschse 115, 235 (1989) pp. 235-240.

H. R. Holzbauer et al. Tenside Deterg. 25, 308 (1988) pp. 308-311.

Domsch et al. Stache Surfactant Science Series, vol. 56, ISBN 0-8247-9394-3; Marcel Dekker Inc. New York, (1996) pp. 501-549.

U. Ploog Seifen-Öle Fette, Waschse 108, (1982) pp. 373-378.

(Continued)

*Primary Examiner*—Milton I Cano
*Assistant Examiner*—Aaron Greso
(74) *Attorney, Agent, or Firm*—David P. LeCroy

(57) ABSTRACT

A fragrance preparation containing 3,7-dimethyloct-6-enenitrile and other compounds described herein is a geranonitrile substitute which has the advantages inherent to geranonitrile, such as fragrance freshness and composition stability but is less objectionable from a toxicological standpoint.

10 Claims, No Drawings

FOREIGN PATENT DOCUMENTS

| | | |
|---|---|---|
| JP | 58217598 | 12/1983 |
| JP | 2004231543 | 8/1992 |
| JP | 4-339896 | 11/1992 |
| WO | WO9218542 | 10/1992 |
| WO | WO9308251 | 4/1993 |
| WO | WO9316110 | 8/1993 |
| WO | WO93/23603 | 11/1993 |
| WO | WO9428030 | 12/1994 |
| WO | WO9507303 | 3/1995 |
| WO | WO9512619 | 5/1995 |
| WO | WO9519953 | 7/1995 |
| WO | WO9519954 | 7/1995 |
| WO | WO9519955 | 7/1995 |
| WO | WO9520029 | 7/1995 |
| WO | WO9520608 | 8/1995 |
| WO | WO9623768 | 8/1996 |
| WO | WO9638528 | 12/1996 |
| WO | WO9926601 | 3/1999 |
| WO | WO03038022 | 5/2003 |

OTHER PUBLICATIONS

O'Lenick et al. HAPPI, Nov. 1986 pp. 70-74.

S. Holzmann et al. Tenside Surfactants Det. vol. 23, (1986) pp. 309-313.

R. Bibo et al. Soap Cosm. Spec. Apr. 1990 pp. 46-50 & 114-122.

K.H. Wallhäußor "Praxis der Sterilisation Desinfektion-Konservierung: Keim-identifizierung-Betriebshygiene" 5th Ed.-stuttgart; New York: Thieme.

P. Finkel SÖFW-Journal vol. 122, (1996) p. 543.

Mackenzie, R.C. and Mitchell, B. D., The Analyst vol. 87 (1962) p. 420-434.

* cited by examiner

GERANONITRILE SUBSTITUTE

CROSS REFERENCE TO RELATED APPLICATIONS

This application is a continuation under 35 U.S.C. §365(c) and 35 U.S.C. §120 of International Application No. PCT/EP2005/011072, filed Oct. 14, 2005. This application also claims priority under 35 U.S.C. §119 of German Application No. DE 10 2004 054620.7, filed Nov. 11, 2004, each of which is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION (1) Field of the Invention

The present invention relates to a fragrance preparation which can be used as an equivalent replacement for the toxicologically disputed geranonitrile. It further relates to the use of said preparation for producing a citrus odor. It relates, furthermore, to various compositions, such as detergents, which comprise a fragrance preparation of this kind.

Many industrial and household products have fragrances added to them in order to mask their intrinsic unpleasant odor and/or for olfactory enhancement of these products or of objects treated with them. For instance, artificial leather can be made to smell like real leather, and thus the value of the product can be raised.

Odorants considered to be fragrances are preferably those which trigger a generally pleasant odor sensation in people and are therefore widely used for the perfuming of industrial and sanitary articles, soaps, cosmetics, bodycare products, and the like. In this sense, fragrances also include essences and aromas. Compounds of this kind are used on a widespread basis to generate good odors or to mask unpleasant odors.

For example, in the case of detergents and the like, fragrances are frequently added which per se in general have no cleaning properties, or comparatively minor cleaning properties, but which have a positive influence on users' sensorial impressions. In the case of detergents, there is a great desire not only for the inherent fragrancing of the product but also for the masking of disruptive secondary odors from the wash liquors. When, in laundering, fragrances are transferred from the detergent to the textile, this is generally perceived by the consumer as being very positive, and the consumer associates the good odor of the laundry with its cleanliness, on noting, for example, that a shirt has a very fresh fragrance. Fragrances, consequently, also have the effect of raising product acceptance.

Room fragrancing products and air fresheners are also important examples of the range of application of the fragrances. The action of the room fragrance in products is predominantly sensorial in nature, and by way of particular fragrance mixtures it is possible to bring about an increase in well-being. Here again, a positive experience may be associated with the good odor, for example, by a user noting that a bathroom in which a room fragrancing product has been placed smells as if freshly clean.

The selection of the fragrances, and their combination, depends above all on what association it is intended to bring about in use. For example, for all products which have to do with laundering or cleaning, it can be advantageous to include citrus fragrances in the combination, since to a large number of consumers these fragrances impart the feeling of fresh cleanliness. Citrus fragrances are widespread in nature. Typical examples are lemon, orange, tangerine, bergamot, grapefruit, lime, etc. Common to all of them is a fresh head note, which a great number of consumers associates with the idea of the aforesaid fresh cleanliness.

A citrus fragrance with high consumer acceptance and high stability in many products is geranonitrile (CAS 5416-66-7; 3,7-dimethyl-2,6-octadienenitrile; BASF). Geranonitrile is used as a stable substitute for common citrus fragrance materials (such as the citrals, for example) in industrial products such as toilet cleaners, for example, as a fragrance, and produces a greatly desired and pleasant citrus fragrance note. Geranonitrile also lends itself well to incorporation into industrial products, such as detergents, and is stable in such products even when, for example, they have a high pH.

But according to new findings (BASF, 2003), geranonitrile possibly has a mutagenic potential. At the present time (2004), therefore, geranonitrile is classed under the EU classification criteria as a category 3 mutagen (M:3). For CMR (CMR=carcinogenic, mutagenic, reprotoxic) substances in category 3 it is necessary to demonstrate that the amounts used are harmless to the consumer.

On the basis of the toxicological data which now exist, there is a concern, in the sense of preventive consumer protection, to replace this compound (geranonitrile) by other odorants and fragrances. There is no known single odorant having an odor profile that corresponds fully to that of geranonitrile.

Consequently the problem addressed by this invention was that of providing a geranonitrile substitute which in typical product applications, such as in detergents, has virtually the exact same odor as geranonitrile but is less objectionable from a toxicological standpoint.

(2) Description of Related Art, Including Information Disclosed Under 37 C.F.R. §§1.97 and 1.98

Not Applicable

BRIEF SUMMARY OF THE INVENTION

This problem has been solved by means of a fragrance preparation comprising 3,7-dimethyloct-6-enenitrile (Cas No. 051566-62-2) and at least one further component selected from a) undecanal isomer mixture, preferably from n-undecanal (Cas No. 112-44-7), linear and branched $C_{11}$ aldehyde (Cas No. 68516-18-7) and 2-methyldecanal (Cas No. 19009-56-4)

b) 2-butyl-4,6-dimethyldihydropyran (Cas No. 024237-00-1), c) 2-benzyl-2-methyl-3-butenenitrile (Cas No. 097384-48-0), d) 2,4-dimethyl-4-phenyltetrahydrofuran (Cas No. 082461-14-1), e) ethylmethoxynorbornane isomer mixture, preferably a mixture of 1-ethyl-3-methoxytricyclo[2.2.1.0-2,6]heptane (Cas No. 31996-78-8) and 2-ethyl-5-methoxybicyclo[2.2.1]heptane (Cas No. 122795-41-9), f) cis-, trans-3-methyl-5-phenyl-2-pentenenitrile [i.e., a methyl-5-phenyl-2-pentenenitrile (cis-, trans-)isomer mixture (Cas. No. 93893-89-1) of (cis)-3-methyl-5-phenylpent-2-enenitrile (Cas No. 53243-59-7) and (trans)-3-methyl-5-phenylpent-2-enenitrile (Cas No. 53243-60-0)], and g) 9-decen-1-ol (Cas No. 013019-22-2).

BRIEF DESCRIPTION OF THE SEVERAL VIEWS OF THE DRAWING(S)

Not Applicable

DETAILED DESCRIPTION OF THE INVENTION

It is preferred for the fragrance preparation to comprise at least two, preferably at least three, advantageously at least four, more advantageously at least five, with further advantageous at least six, and in particular, all of the further components (a) to (g).

It is preferred for the fragrance preparation to contain, in addition to the 3,7-dimethyloct-6-enenitrile, at least 2-benzyl-2-methyl-3-butenenitrile, cis-, trans-3-methyl-5-phenyl-2-pentenenitrile, and 2-butyl-4,6-dimethyldihydropyran. It is even more advantageous if 9-decen-1-ol is present as well. It is even more advantageous still if undecanal isomer mixture, 2,4-dimethyl-4-phenyltetrahydrofuran and/or ethylmethoxynorbornane isomer mixture are included as well.

All of the aforementioned components are also available commercially: e.g., 3,7-dimethyloct-6-enenitrile as "Citronellyl Nitrile" ex Symrise, and (a) undecanal isomer mixture of n-undecanal, linear+ branched $C_{11}$ aldehyde, and 2-methyldecanal as "Aldehyde 11-11" ex Cognis Deutschland,
(b) 2-butyl-4,6-dimethyldihydropyran as "Gyranes" ex Quest International,
(c) 2-benzyl-2-methyl-3-butenenitrile as "Citrowanil B" ex Symrise,
(d) 2,4-dimethyl-4-phenyltetrahydrofuran as "Rhubafuran" ex Quest,
(e) ethylmethoxynorbornane isomer mixture as "Neoproxen" ex International Flavors & Fragrances,
(f) cis-, trans-3-methyl-5-phenyl-2-pentenenitrile as "Citronitrile" ex Symrise,
(g) 9-decen-1-ol as "Rosalva" ex International Flavors & Fragrances.

In one preferred embodiment the fragrance preparation comprises 5-95% by weight, preferably 10-90% by weight, in particular, 45-60% by weight of 3,7-dimethyloct-6-enenitrile, based on the overall fragrance preparation.

In one preferred embodiment the fragrance preparation comprises 2-benzyl-2-methyl-3-butenenitrile, advantageously in amounts of 0.01-65% by weight, preferably 0.5-25% by weight, in particular, 1-15% by weight, based on the overall fragrance preparation.

In one preferred embodiment the fragrance preparation comprises 2-butyl-4,6-dimethyldihydropyran, advantageously in amounts of 0.1-45% by weight, preferably 0.5-35% by weight, in particular, 1-25% by weight, based on the overall fragrance preparation.

In one preferred embodiment the fragrance preparation comprises cis-, trans-3-methyl-5-phenyl-2-pentenenitrile, advantageously in amounts of 0.1-25% by weight, preferably 0.5-20% by weight, in particular, 1-10% by weight, based on the overall fragrance preparation.

In one preferred embodiment the fragrance preparation comprises 9-decen-1-ol, advantageously in amounts of 0.01-25% by weight, preferably 0.1-10% by weight, in particular, 1-5% by weight, based on the overall fragrance preparation.

In one preferred embodiment the fragrance preparation comprises undecanal isomer mixture, advantageously in amounts of 0.01-25% by weight, preferably 0.1-15% by weight, in particular, 1-10% by weight, based on the overall fragrance preparation.

In one preferred embodiment the fragrance preparation comprises 2,4-dimethyl-4-phenyltetrahydrofuran, advantageously in amounts of 0.01-15% by weight, preferably 0.1-10% by weight, in particular, 1-5% by weight, based on the overall fragrance preparation.

In one preferred embodiment the fragrance preparation comprises ethylmethoxynorbornane isomer mixture, advantageously in amounts of 0.01-10% by weight, preferably 0.1-5% by weight, in particular, 1-3% by weight, based on the overall fragrance preparation.

In one preferred embodiment the fragrance preparation of the invention is distinguished by the fact that i) the weight ratio of 3,7-dimethyloct-6-enenitrile to undecanal isomer mixture is 300:1 to 1:5, preferably 200:1 to 1:3, in particular, 100:1 to 1:2 and/or
ii) the weight ratio of 3,7-dimethyloct-6-enenitrile to 2-butyl-4,6-dimethyldihydropyran 200:1 to 1:9, preferably 100:1 to 1:4, in particular, 50:1 to 1:2 and/or
iii) the weight ratio of 3,7-dimethyloct-6-enenitrile to 2-benzyl-2-methyl-3-butenenitrile is 200:1 to 1:13, preferably 70:1 to 1:5, in particular, 50:1 to 1:2 and/or
iv) the weight ratio of 3,7-dimethyloct-6-enenitrile to 2,4-dimethyl-4-phenyltetrahydrofuran is 300:1 to 1:13, preferably 200:1 to 1:5, in particular, 100:1 to 1:2 and/or
v) the weight ratio of 3,7-dimethyloct-6-enenitrile to ethyl methoxynorbornane isomer mixture is 400:1 to 1:2, preferably 300:1 to 2:3, in particular, 200:1 to 1:1 and/or
vi) the weight ratio of 3,7-dimethyloct-6-enenitrile to cis-, trans-3-methyl-5-phenyl-2-pentenenitrile is 200:1 to 1:5, preferably 70:1 to 1:3, in particular, 40:1 to 1:2 and/or
vii) the weight ratio of 3,7-dimethyloct-6-enenitrile to 9-decen-1-ol is 400:1 to 1:5, preferably 300:1 to 1:3, in particular, 200:1 to 1:2.

The best embodiment at present in terms of an odor impression very largely equivalent to that of geranonitrile in conjunction with a high stability of constitution is composed of a fragrance preparation which as well as the 3,7-dimethyloct-6-enenitrile comprises all of further components (a) to (g), preferably in the aforementioned proportions. Such a combination of the stated fragrances produces an outstanding geranonitrile substitute. Advantageously it is no longer possible for a nonexpert, i.e., a typical consumer, to distinguish the fragrance of such a substitute from that of geranonitrile in the product, a detergent for example. Even perfumers with a trained and finely differentiating sense of smell are, advantageously, virtually unable to distinguish the fragrance impression of the substitute-containing perfume oil from the fragrance impression of the geranonitrile-containing perfume oil in typical products, detergents for example. Advantageously the substitute can be incorporated without difficulties into technical compositions, such as detergents, and is stable in such compositions, even on prolonged storage.

A fragrance preparation of the invention need not be restricted to the stated ingredients. The fragrance preparation may advantageously include further, typical constituents, examples being essential oils, flower oils, extracts from plant and animal drugs, absolutes, resinoids, and odorants isolated from natural products, chemically modified (semisynthetic) odorants, and odorants obtained by purely synthetic means, and the like.

The fragrance preparation can advantageously be diluted as desired with solvents. A very preferred solvent is ethanol, though where appropriate, dilution can also be carried out with dipropylene glycol, or else water, preferably together with emulsifiers, in order to set a desired concentration.

The present specification further provides a composition comprising fragrance that comprises a fragrance preparation of the invention. Reference below to a composition of the invention, unless indicated otherwise, is to a fragrance-comprising composition of this kind that comprises a fragrance preparation of the invention.

A fragrance for the purposes of this invention is any odorant, hence including aromas and essences, particularly those odorants which trigger a substantially positive odor sensation in people.

In one preferred embodiment the composition comprising fragrance is a textile treatment product, an ironing aid, a cleaning cloth, a laundry detergent, a cleaning product, in particular, for hard and/or soft surfaces, a household cleaner, a care product, a wash care product, a laundry care product, a room fragrancer, and air freshener, a conditioner, a colorant, a fabric conditioner, a conditioning substrate, a pharmaceutical, a crop protection product, a polish, a food, a cosmetic product, a fertilizer, a building material, an adhesive, a bleach, a decalcifier, an autocare product, floorcare product, cookercare product, leathercare product or furniture care product, a scourer, a disinfectant, a fragrancer, a mold remover and/or a precursor of the aforementioned products.

Particular preference is given to detergents and to any care products, and also to the air fresheners and room fragrancers.

The preferred cleaning products include the toilet cleaners or lavatory cleaners, in other words, products for cleaning lavatory bowls and urinals, these products being supplied preferably in the form of powders, blocks, tablets or liquids, preferably gels. Besides other typical ingredients such as surfactants, they generally include organic acids e.g., citric acid and/or lactic acid) or sodium hydrogen sulfate, amidosulfuric acid or phosphoric acid for removing limescale or urine scale.

The preferred cleaning products also include the pipe-cleaning products or drain cleaners. These are preferably strongly alkaline products which serve in general to remove pipe blockages comprising organic materials—such as hair, fat, food residues, soap deposits, etc. Additions of Al powder or Zn powder may serve for the formation of $H_2$ gas with an effervescence effect. Possible ingredients are commonly alkalis, alkaline salts, oxidizing agents, and neutral salts. Supply forms in powder form preferably also include sodium nitrate and sodium chloride. Pipe-cleaning products in liquid form may preferably also include hypochlorite. There are also enzyme-based drain cleaners as well. Acidic products are likewise possible.

The preferred cleaning products also include the universal or all-purpose or general-purpose cleaners. These are cleaners which can be used universally for all hard surfaces in the household and in commerce that can be wiped down wet or damp. Generally speaking, they are neutral or slightly alkaline or slightly acidic products, especially liquid products. All-purpose or general-purpose cleaners generally contain surfactants, builders, solvents and hydrotropes, dyes, preservatives, etc.

There are also all-purpose cleaners with special disinfectant properties. They additionally include active antimicrobial ingredients (e.g., aldehydes, alcohols, quaternary ammonium compounds, amphoteric surfactants, triclosan).

The preferred cleaning products also include the sanitary cleaners. These are products for cleaning in bath and toilet. The alkaline sanitary cleaners are used preferably for removing fatty soiling, whereas the acidic sanitary cleaners are employed in particular, for removing limescale. Sanitary cleaners advantageously also have a considerable disinfectant action, particularly the strongly alkaline sanitary cleaners that contain chlorine.

The preferred cleaning products also include the oven cleaners or grill cleaners which are supplied advantageously in the form of gels or foam sprays. They generally serve for removing burnt-on or carbonized food residues. Oven cleaners are preferably given a strongly alkaline formulation using, for example, sodium hydroxide, sodium metasilicate, 2-aminoethanol. In addition they generally contain anionic and/or nonionic surfactants, water-soluble solvents, and, in some cases, thickeners such as polycarboxylates and carboxymethylcellulose.

The preferred cleaning products also include the metal polishes. These are cleaners for particular types of metal such as stainless steel or silver. Stainless steel cleaners preferably contain, besides acids (preferably up to 3% by weight, e.g., citric acid, lactic acid), surfactants (in particular, up to 5% by weight, preferably nonionic and/or anionic surfactants), and water, solvents as well (preferably up to 15% by weight) to remove fatty soiling, and also further compounds such as thickeners and preservatives. Very fine polishing structures are included, furthermore, in products for preferably bright stainless steel surfaces. Silver polishes, in turn, are preferably given an acidic formulation. In particular, for removing black deposits of silver sulfide they contain, preferably, complexing agents (e.g., thiourea, sodium thiosulfate). Typical supply forms are polishing cloths, dipping baths, pastes, and liquids. Dark discolorations (oxide layers) are removed using copper cleaners and nonferrous-metal cleaners (e.g., for brass and bronze). They generally have a weakly alkaline formulation (preferably with ammonia) and in general contain polishing agents and also, preferably, ammonium soaps and/or complexing agents.

The preferred cleaning products also include the glass cleaners and window cleaners. These products serve preferably to remove dirt, especially greasy dirt, from glass surfaces. Preferably they contain compounds such as anionic and/or nonionic surfactants (in particular, up to 5% by weight), ammonia and/or ethanolamine (in particular, up to 1% by weight), ethanol and/or 2-propanol, glycol ethers (in particular, 10-30% by weight), water, preservatives, dyes, anti-misting agents, etc.

The preferred cleaning products also include all special-purpose cleaning products, examples being those for glass-ceramic hobs, and also carpet cleaners and stain removers.

The preferred autocare products include paint preservers, paint polishes, paint cleaners, wash preservers, shampoos for auto washing, auto-wash and wax products, polishes for trim metals, protective films for trim metals, plastics cleaners, tar removers, screen cleaners, engine cleaners, etc.

Preferred cosmetic products are preferably (a) cosmetic skincare products, especially bath products, skin washing and cleansing products, skincare products, eye makeup, lip care products, nail care products, intimate care products, foot care products (b) cosmetic products with specific effects, especially sunscreens, tanning products, de-pigmenting products, deodorants, antiperspirants, hair removers, shaving products, perfumes, (c) cosmetic dental-care products, especially dental and oral care products, toothcare products, cleaners for dental prostheses, adhesives for dental prostheses, (d) cosmetic hair care products, especially hair shampoos, hair care products, hair setting products, hair-shaping products, hair coloring products.

Particular preference is also given to any textile treatment products, such as detergents or fabric conditioners, for example, in either liquid or solid form.

Particular preference is also given to the air fresheners and room fragrancers. Products of this kind contain preferably volatile and usually pleasant-smelling compounds which advantageously can even in very small amounts mask unpleasant odors. Air fresheners for living areas contain, in particular, natural and synthetic essential oils such as pine needle oils, citrus oil, eucalyptus oil, lavender oil, etc., in amounts for example of up to 50% by weight. As aerosols they tend to contain smaller amounts of such essential oils, by way of example less than 5% or less than 2% by weight, but additionally include, preferably, compounds such as acetaldehyde (in particular, <0.5% by weight), isopropyl alcohol (in particular, <5% by weight), mineral oil (in particular, <5% by weight), and propellants. Other presentation forms include sticks and blocks. They are produced preferably using a gel concentrate comprising essential oils. Advantageously it is also possible to add formaldehyde (for preservation) and chlorophyll (preferably <5% by weight), and also further ingredients.

Air fresheners are not, however, restricted to living spaces, but may also be intended for autos, cupboards, dishwashers, refrigerators or shoes, and even their use in vacuum cleaners is a possibility. In the household (e.g., in cupboards), for example, in addition to the odor improvers, disinfectants as well are employed, containing preferably compounds such as calcium phosphate, talc, stearin, and essential oils, these products taking the form, for example, of sachets.

According to one preferred embodiment the composition comprising fragrance comprises a weight fraction of the fragrance preparation of the invention of $\geqq 10^{-6}$% by weight and $\leqq$50% by weight, preferably $\geqq 10^{-5}$% by weight and $\leqq$40% by weight, preferentially $\geqq 10^{-4}$% by weight and $\leqq$30% by weight, more preferably $\geqq 10^{-3}$% by weight and $\leqq$20% by weight, more preferably still $\geqq 10^{-2}$% by weight and $\leqq$10% by weight, and most preferably $\geqq$0.03% by weight and $\leqq$5% by weight, based on the total weight of the composition.

According to a further preferred embodiment the composition comprising fragrance is at least partly in solid form, in gel form, in foam form and/or liquid form. If it is present in solid form, it then takes the form, preferably, of granules, powders, tablets with at least one phase and/or pressed tablets.

It is an advantage of the invention that the fragrance preparation is very stable. In the various matrices and compositions as well, such as cleaning products or detergents, for example, the fragrance preparation is stable and the fragrance of the fragranced composition is also stable on storage.

In a further preferred embodiment the composition comprising fragrance comprises, in addition to the fragrance preparation, at least one further fragrance, advantageously two or more further fragrances, preferably with a total weight content of these further fragrances of >0% by weight and <50% by weight, preferably $\geqq 10^{-6}$% by weight and $\leqq$40% by weight, preferentially $\geqq 10^{-5}$% by weight and $\leqq$30% by weight, more preferably $\geqq 10^{-4}$% by weight and $\leqq$20% by weight, more preferably still $\geqq 10^{-3}$% by weight and $\leqq$15% by weight, more preferably still $\geqq 10^{-2}$% by weight and $\leqq$10% by weight, and most preferably $\geqq 10^{-1}$% and $\leqq$5% by weight, based on the total weight of the composition.

According to a further preferred embodiment the additional fragrance or fragrances in the composition comprising fragrance are selected from the group comprising fragrances with fragrance notes of green notes, citrus notes, lavender notes, flowery notes, aldehyde notes, chypre notes, fougere notes, spice notes, oriental notes, wood notes, tobacco notes and/or leather notes.

According to a further preferred embodiment the additional fragrance or fragrances in the composition comprising fragrance are selected from the group comprising fragrances of natural or synthetic origin, preferably relatively volatile fragrances, relatively high-boiling fragrances, solid fragrances and/or firmly adhering fragrances.

Through an appropriate selection of the additional fragrances it is possible in the compositions of the invention to influence not only the product odor but also the post-application odor of treated objects. The post-application odor is the odor which appears after the end of an application, such as of a cleaning operation and care operation, this fragrance taking the form, for example, of the laundry fragrance or textile fragrance.

It is an advantage of the invention that the fragrance preparation of the invention, both alone and when blended with further fragrances, gives rise to a fragrance-intensifying effect, i.e., the perceived fragrance on the fragranced object becomes more intense and has a fresher effect.

For the latter, post-application odor impression, i.e., for the objects fragranced indirectly, the use of relatively firmly adhering odorants is advantageous, whereas for simple product fragrancing it is also possible with advantage to use relatively volatile odorants.

The composition of the invention can be used for fragrancing an article, a surface or a room, preferably textile fabrics, household surfaces, shoes, waste containers, recycling containers, air, sizable household appliances, cat litter, pets, pet sleeping facilities, especially articles of clothing, carpets, rugs, curtains, drapes, upholstered furniture, bed linen, tents, sleeping bags, auto seats, auto carpets, auto interior textile trim, counters, walls, floors, bathroom surfaces, kitchen surfaces, refrigerators, chest freezers, washing machines, dishwashers, tumble dryers, ovens, and microwaves, directly or indirectly. The composition in this case can be applied in any desired form, as for example by spraying using a spray applicator.

Firmly adhering odorants which can be used for the purposes of the present invention are, for example, essential oils such as angelica root oil, anise oil, arnica flower oil, basil oil, bay oil, bergamot oil, champaca flower oil, noble fir oil, noble fir cone oil, elemy oil, eucalyptus oil, fennel oil, spruce needle oil, galbanum oil, geranium oil, ginger grass oil, guaiac wood oil, gurjun balsam oil, helichrysum oil, ho oil, ginger oil, iris oil, cajeput oil, calmus oil, camomile oil, camphor oil, canaga oil, cardamom oil, cassia oil, pine needle oil, copaiva balsam oil, coriander oil, spearmint oil, caraway oil, cumin oil, lavender oil, lemongrass oil, lime oil, mandarin oil, melissa oil, muscat kernel oil, myrrh oil, oil of cloves, neroli oil, niaouli oil, olibanum oil, orange oil, origanum oil, palmarosa oil, patchouli oil, peru balsam oil, petit grain oil, pepper oil, peppermint oil, pimento oil, pine oil, rose oil, rosemary oil, sandalwood oil, celery oil, spike oil, star anise oil, terpentine oil, thuja oil, thyme oil, verbena oil, vetiver oil, juniper berry oil, wormwood oil, wintergreen oil, ylang-ylang oil, hyssop oil, cinnamon oil, cinnamon leaf oil, citronella oil, lemon oil, and cypress oil.

However, higher-boiling or solid odorants of natural or synthetic origin can also be used for the purposes of the present invention as firmly adhering odorants or firmly adhering odorant mixtures, i.e., fragrances. These compounds include the compounds named below and mixtures thereof: ambrettolide, α-amylcinnamaldehyde, anethole, anisaldehyde, anisyl alcohol, anisole, methyl anthranilate, acetophenone, benzylacetone, benzaldehyde, ethyl benzoate, benzophenone, benzyl alcohol, benzyl acetate, benzyl benzoate, benzyl formate, benzyl valerate, borneol, bornyl acetate, α-bromostyrene, n-decyl aldehyde, n-dodecyl aldehyde, eugenol, eugenol methyl ether, eucalyptol, farnesol, fenchone, fenchyl acetate, geranyl acetate, geranyl formate, heliotropin, methyl heptyne carboxylate, heptaldehyde, hydroquinone dimethyl ether, hydroxycinnamaldehyde, hydroxycinnamal alcohol, indole, irone, isoeugenol, isoeugnol methyl ether, isosafrol, jasmone, camphor, carvacrol, carvone, p-cresol methyl ether, coumarin, p-methoxyacetophenone, methyl n-amyl ketone, methyl methylanthranilate, p-methylacetophenone, methylchavicol, p-methylquinoline, methyl β-naphthyl ketone, methyl-n-nonylacetaldehyde, methyl n-nonyl ketone, muscone, β-naphthol ethyl ether, β-naphthol methyl ether, nerol, nitrobenzene, n-nonylaldehyde, nonyl alcohol, n-octylaldehyde, p-oxyacetophenone, pentadecanolide, β-phenylethyl alcohol, phenylacetaldehyde dimethyl acetal, phenylacetic acid, pulegone, safrol, isoamyl salicylate, methyl salicylate, hexyl salicylate, cyclohexyl salicylate, santalol, skatole, terpineol, thymene, thymol, γ-undelactone, vanillin, veratrum aldehyde, cinnamaldehyde, cinnamal alcohol, cinnamic acid, ethyl cinnamate, and benzyl cinnamate.

The more readily volatile fragrances include, in particular, the lower-boiling odorants of natural or synthetic origin, which can be used alone or in mixtures.

Examples of more readily volatile fragrances are alkyl isothiocyanates (alkyl mustard oils), butanedione, limonene, linalool, linayl acetate and propionate, menthol, menthone, methyl-n-heptenone, phellandrene, phenylacetaldehyde, terpinyl acetate, citral, and citronellal.

According to a further preferred embodiment the additional fragrance or fragrances in the composition comprising fragrance are selected from the group encompassing:

- essence of fruits, fruit parts and/or other plant parts, preferably herbs, drugs, essential oils obtained therefrom, preferably terpene-free oils; and/or
- artificial essences, preferably from synthetic odor compounds and/or flavor compounds, more preferably vanillin, menthol, diacetyl and/or eucalyptol; and/or
- aromas, preferably essential oils, anise oil, star anise oil, bitter almond oil, eucalyptus oil, fennel oil, peppermint oil, lemon oil, wintergreen oil, clove oil, menthol and/or carraway oil; and/or
- synthetic odorant compounds of ester type, preferably benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl methyl phenyl glycinate, allyl cyclohexylpropionate, styrallyl propionate and/or benzyl salicylate; and/or
- synthetic odorant compounds of ether type, preferably benzyl ethyl ether; and/or
- synthetic odorant compounds of aldehyde type, preferably linear alkanals having 8-18 carbon atoms, citral, citronellal, citronellyloxyacetaldehyde, cyclamenaldehyde, hydroxycitronellal, lilial and/or bourgenal; and/or
- synthetic odorant compounds of ketone type, preferably ionones, isomethylionone and/or methyl cedryl ketone; and/or
- synthetic odorant compounds of alcohol type, preferably anethol, citronellol, eugenol, geraniol, linalool, phenylethyl alcohol and/or terpineol; and/or
- synthetic odorant compounds of hydrocarbon type, preferably terpenes, more preferably limonene and piniene; and/or
- natural odorant mixtures from plant sources, preferably pine, citrus, jasmine, patchouli, rose or ylang-ylang oil, clary sage oil, camomile oil, clove oil, balm oil, mint oil, cinnamon leaf oil, lime blossom oil, juniper berry oil, vetiver oil, olibanum oil, galbanum oil, labdanum oil, orange blossom oil, neroliol, orange peel oil and/or sandalwood oil.

It can be advantageous to accelerate or retard the release of the fragrances, i.e., of the fragrance preparation and/or of the other fragrances, as a function of the particular end use. For example, when employing compositions of the invention in a laundering or cleaning liquor, it can be advantageous to release the fragrances only at the end of or even only after the application, since in such cases it may be desirable for the fragrances only to develop fully on the treated article.

Alternatively it may be desirable, as when cleaning hard surfaces, for example, for the fragrances, i.e., the fragrance preparation and/or the other fragrances, to develop at a substantially uniform rate over the duration of the cleaning step.

When the fragrances are used in a tumble dryer, for example, it may be the desired aim that the fragrances, i.e., the fragrance preparation and/or the other fragrances, are released only at the end of the drying operation and are also still perceptible by the user when the laundry is removed, so as to give an impression of "fresh" laundry.

For the accelerated or retarded release of fragrances, especially of the fragrance preparations of the invention, it is possible to employ all of the methods known in the prior art, provided they appear suitable to the skilled worker.

In the prior art there are, for instance, proposals to attach fragrances chemically to support substances, such as polymers, thereby producing, preferably, a retardation of fragrance release.

Inventively suitable support substances, also referred to as controlled release systems, to which the fragrances can be chemically attached, are, for example, siloxanes, from which these fragrances are slowly released by acidic hydrolysis.

Ortho-silicic esters are described for example in U.S. Pat. No. 3,215,719 (Dan River Mills), hereby fully incorporated by reference.

Further inventively suitable silicon compounds are described in German Patent Nos. DE 2844789 and DE 30 03 494 (Dow Corning), hereby fully incorporated by reference.

Published International Application No. WO 96/38528 (Procter & Gamble), hereby fully incorporated by reference, specifies betaine esters and polymeric betaine esters in which the quaternary ammonium groups are linked to one another via polyalkylene chains, and which are likewise suitable for esterification with the inventively suitable fragrances.

Particularly suitable is the use of silicon compounds substantially modified with organic radicals, which allow a long-lasting fragrance impression on textile sheetlike structures, fibers and/or yarns.

Also particularly suitable in this context is a cyclodextrin derivative of the formula $A[-Z^1—X—Z^2-(EO/PO)_n—R^1]_m$, in which A is an m-valent cyclodextrin radical formed from a cyclodextrin molecule by removal of m hydroxyl groups, $Z^1$=O, S or $NR^2$, $R^2$ being hydrogen, an alkyl group of 1 to 8 carbon atoms, an aryl group of 6 to 20 carbon atoms or a radical —C(O)—$R^3$, in which $R^3$ is an alkyl radical having 1 to 20 carbon atoms, X—$Z^2$ is a bond, or X is a divalent radical of a difunctional molecule one of whose functional groups, $F^1$, is able to react with a cyclodextrin $A(\text{-OH})_m$ or with a cyclodextrin derivative $A(\text{-O-G})_m$, in which O-G is a leaving group such as the toluenesulfonyl group, for example, and the other of whose functional groups, $F^2$ is able to react with a hydroxyl, mercapto or amino group, in each case with formation of a covalent bond, and $Z^2$ has the same definitions as $Z^1$, it being possible for $Z^1$ and $Z^2$ to be alike or different, and where in formula (I) the divalent radical X is linked via $F^1$ to $Z^1$ and via $F^2$ to $Z^2$, $(EO/PO)_n$ is a divalent alkoxylate radical which is linked via a carbon atom to $Z^2$ and via an oxygen atom to $R^1$, and which consists of 1 to 150 ethylene glycol and/or propylene glycol units, $R^1$ is hydrogen, an alkyl radical of 1 to 20 carbon atoms, an aryl or aralkyl radical of 6 to 25 carbon atoms, or is the sulfate radical, and m=1, 2 or 3, it not being possible for the cyclodextrin derivative of the formula (I) to be mono- or dihydroxypropylcyclodextrin.

Cyclodextrin derivatives of this kind are outstandingly suitable for providing fibers temporarily with active-ingredient-binding properties and/or active-ingredient-releasing properties. By temporary finishing is meant that the finish remains for a certain time on a textile, for example, such as during the wearing of an article of textile clothing, and can be removed again with re-establishment of the original condition of the fiber, in particular, by means of a simple washing and/or cleaning process. This is thought to be made possible by virtue of the fact that these cyclodextrin derivatives do not react with the fiber, forming covalent bonds, but instead merely cling to the fiber by way, for example, of polar and/or van de Waals interactions. By active ingredients in this context are meant molecules which can be bound by the free cyclodextrin derivative of the invention or by the cyclodextrin derivative of the invention located on or in the fiber. Active ingredients are, in particular, those compounds which form host-guest complexes with cyclodextrins. In particular, the active ingredient is an odorant, preferably odorants of the kind corresponding to the fragrance preparation of the invention.

Suitable support substances for the fragrances may preferably be selected from the group encompassing polymers, siloxanes, silicon compounds modified with organic radicals, betaines, paraffins, surfactants, especially ethoxylated fatty alcohols, fatty acids, silicone oils and/or fatty alcohol, preferably lipophilic substances, particular preference being given to lipophilic substances with a melting point above 25° C.

Support substances which are particularly in accordance with the invention for the fragrances which can be used in accordance with the invention are meltable or softenable substances from the group of waxes, paraffins, polyalkylene glycols, and the like. Meltable of softenable substances preferably have a melting range which is situated between about 45° C. and about 75° C. In the present case this means that the melting range occurs within the stated temperature interval, and does not denote the breadth of the melting range.

The term “waxes” is applied to a range of natural or synthetic substances which melt without decomposition, generally at above 40° C., and are of comparatively low viscosity, without stringing, even at just a little above the melting point. They have a highly temperature-dependent consistency and solubility. According to their origin, the waxes are divided into three groups: the natural waxes, chemically modified waxes, and the synthetic waxes.

The natural waxes include, for example, plant waxes such as candelilla wax, carnauba wax, Japan wax, esparto grass wax, cork wax, guaruma wax, rice germ oil wax, sugar cane wax, ouricury wax, or montan wax, animal waxes such as beeswax, shellac wax, spermaceti, lanolin (wool wax), or uropygial grease, mineral waxes such as ceresin or ozokerite (earth wax), or petrochemical waxes such as petrolatum, paraffin waxes or microcrystalline waxes.

The chemically modified waxes include, for example, hard waxes such as montan ester waxes, sassol waxes, or hydrogenated jojoba waxes.

By synthetic waxes are meant, in general, polyalkylene waxes or polyalkylene glycol waxes. As meltable or softenable substances for the materials which harden by cooling it is also possible to use compounds from other classes of substance which meet the stated requirements in terms of softening point. Examples of synthetic compounds which have proven suitable are higher esters of phthalic acid, especially dicyclohexyl phthalate, which is available commercially under the name Unimoll® 66 (Bayer AG). Also suitable are synthetically prepared waxes from lower carboxylic acids and fatty alcohols, an example being dimyristyl tartrate, which is available under the name Cosmacol® ETLP (Condea). Conversely, synthetic or partially synthetic esters of lower alcohols with fatty acids from natural sources may also be used. This class of substance includes, for example, Tegin® 90 (Goldschmidt), a glyceryl monostearate palmitate. Shellac as well, for example, Schellack-KPS-Dreiring-SP (Kalkhoff GmbH), may be used inventively as a meltable or softenable substance.

Likewise counted among the waxes in the context of the present invention are, for example, the so-called wax alcohols. Wax alcohols are relatively high molecular mass, water-insoluble fatty alcohols having in general from about 22 to 40 carbon atoms. The wax alcohols occur, for example, in the form of wax esters of relatively high molecular mass fatty acids (wax acids) as a principal constituent of many natural waxes. Examples of wax alcohols are lignoceryl alcohol (1-tetracosanol), cetyl alcohol, myristyl alcohol, and melissyl alcohol. Other meltable and softenable substances are the wool wax alcohols, by which are meant triterpenoid and steroid alcohols, an example being lanolin, which is available under the commercial designation Argowax® (Pamentier & Co.), for example. Likewise possible for use, at least proportionally, as a constituent of the meltable or softenable substances are, in the context of the present invention, fatty acid glycerol esters or fatty acid alkanolamides, and also, if desired, water-insoluble or only sparingly water-soluble polyalkylene glycol compounds.

Particularly preferred meltable or softenable support materials are those from the group of polyethylene glycols (PEG) and/or polypropylene glycols (PPG), preference being give to polyethylene glycols with molar masses between 1,500 and 36,000, particular preference to those of molar masses from 2,000 to 6,000, and especial preference to those with molar masses from 3,000 to 5,000. Corresponding processes which are characterized in that the plastically deformable material or materials comprises or comprise at least one substance from the group of polyethylene glycols (PEG) and/or polypropylene glycols (PPG) are preferred.

Particular preference is given in this context to materials which as sole meltable or softenable substances contain propylene glycols (PPG) and/or polyethylene glycols (PEG). Polypropylene glycols useful in accordance with the invention (PPG for short) are polymers of propylene glycol which satisfy the general formula below, it being possible for n to adopt values between 10 and 2,000. Preferred PPG have molar masses between 1,000 and 10,000, and values for n, correspondingly, of between 17 and approximately 170.

Polyethylene glycols (PEG for short) which can be used with preference in accordance with the invention as polymeric support materials are polymers of ethylene glycol which satisfy the general formula $H—(O—CH_2—CH_2)_n—OH$, it being possible for n to adopt values between 20 and about 1,000. The above-mentioned preferred molecular weight ranges correspond to preferred ranges of the value n in formula IV of 30 to 820, in particular, of 34 to 818, more preferably of 40 to 150, in particular, of 45 to 136, and more preferably still of 70 to 120, in particular, of 68 to 113.

According to a further preferred embodiment of the invention the composition comprising fragrance comprises supported fragrance, the support material or materials being selected from the group encompassing polymers, siloxanes, silicon-containing compounds modified with organic radicals, betaines, paraffins, surfactants, especially ethoxylated fatty alcohols, fatty acids, silicone oils and/or fatty alcohol, preferably lipophilic substances, particular preference being given to lipophilic substances with a melting point above 25° C. In this context it is possible not only for the fragrance preparation of the invention but also for the additional fragrance or fragrances to be supported.

According to a further preferred embodiment for the composition comprising fragrance, the ratio of fragrance(s) to support substance(s) in the case of a supported fragrance is in the range from 20:1 to 1:10, preferably 5:1 to 10:1, and preferentially 3:1.

In a further preferred embodiment the meltable and softenable support substances which can be used in accordance with the invention predominantly comprise paraffin wax. This means that at least 50% by weight of the total meltable or softenable substances present, preferably more, is composed of paraffin wax. Particularly suitable are paraffin wax contents (based on the total amount of meltable or softenable substances) of about 60%, about 70% or about 80% by weight, particular preference being given to even higher fractions of, for example, more than 90% by weight. In one particular embodiment of the invention the total amount of meltable or softenable substances used in at least one material is composed exclusively of paraffin wax.

Paraffin waxes have the advantage over the other natural waxes mentioned, for the purposes of the present invention, that in an alkaline cleaning-product environment there is no hydrolysis of the waxes (as is to be expected, for example, with the wax esters), since paraffin wax contains no hydrolyzable groups.

Paraffin waxes are composed predominantly of alkanes, along with small fractions of isoalkanes and cycloalkanes. The paraffin which can be used in accordance with the invention preferably contains essentially no constituents having a melting point of more than 70° C., more preferably of more than 60° C. Fractions of high-melting alkanes in the paraffin may, if the melting temperature in the cleaning product liquor goes below this limit, leave unwanted wax residues on the surfaces to be cleaned or on the product to be cleaned. Wax residues of this kind lead in general to an unattractive appearance of the cleaned surface and ought therefore to be avoided.

Meltable or softenable support substances or support-substance mixtures for preferred processing comprise at least one paraffin wax having a melting range of 50° C. to 60° C., preferred processes being characterized in that the deformable material(s) comprise(s) a paraffin wax having a melting range of 50° C. to 55° C.

Preferred support substances suitable for use as fragrances may also be selected from the group of the water-soluble polymers, of which only the most important will be listed: water-soluble nonionic polymers (polyvinylpyrrolidones, vinylpyrrolidone/vinyl ester copolymers, cellulose ethers); water-soluble amphoteric polymers (alkylacrylamide/acrylic acid copolymers, alkylacrylamide/methacrylic acid copolymers, alkylacrylamide/methyl-methacrylic acid copolymers, alkylacrylamide/acrylic acid/alkylaminoalkyl(meth)acrylic acid copolymers, alkylacrylamide/methacrylic acid/alkylaminalkyl(meth)acrylic acid copolymers, alkylacrylamide/methyl-methacrylic acid/alkylamino-alkyl(meth)acrylic acid copolymers, alkylacrylamide/alkyl methacrylate/alkylaminoethyl methacrylate/alkyl methacrylate copolymers; copolymers of unsaturated carboxylic acids, cationically derivatized unsaturated carboxylic acids, where appropriate, further ionic or nonionic monomers; water-soluble zwitterionic polymers (acrylamidoalkyltrialkylammonium chloride/acrylic acid copolymers and their alkali metal salts and ammonium salts, acrylamidoalkyltrialkylammonium chloride/methacrylic acid copolymers and their alkali metal salts and ammonium salts, methacroylethylbetaine/methacrylate copolymers); water-soluble anionic polymers (vinyl acetate/crotonic acid copolymers, vinylpyrrolidone/vinyl acrylate copolymers, acrylic acid/ethyl acrylate/N-tert-butylacrylamide terpolymers, graft polymers of vinyl esters, esters of acrylic acid or methacrylic acid alone or in a mixture, copolymerized with crotonic acid, acrylic acid or methacrylic acid with polyalkylene oxides and/or polyalkylene glycols); grafted and crosslinked copolymers (from the copolymerization of a) at least one monomer of nonionic type, b) at least one monomer of ionic type, c) of polyethylene glycol, and d) of a crosslinker; copolymers obtained by copolymerizing at least one monomer from each of the three following groups: a) esters of unsaturated alcohols and short-chain saturated carboxylic acids and/or esters of short-chain saturated alcohols and unsaturated carboxylic acids, b) unsaturated carboxylic acids, c) esters of long-chain carboxylic acids and unsaturated alcohols and/or esters of the carboxylic acids from the group of saturated or unsaturated, linear or branched $C_{8-18}$ alcohols; terpolymers of crotonic acid, vinyl acetate and an allyl or methallyl ester; tetrapolymers and pentapolymers of a) crotonic acid or allyloxyacetic acid, b) vinyl acetate or vinyl propionate, c) branched allyl or methallyl esters, d) vinyl ethers, vinyl esters or linear allyl or methallyl esters; crotonic acid copolymers with one or more monomers from the group of ethylene, vinylbenzene, vinyl methyl ether, acrylamide and the water-soluble salts thereof; terpolymers of vinyl acetate, crotonic acid and vinyl esters of a saturated aliphatic monocarboxylic acid branched in x position; water-soluble cationic polymers (quaternized cellulose derivatives, polysiloxanes with quaternary groups, cationic guar derivatives, polymeric dimethyldiallylammonium salts and their copolymers with esters and amides of acrylic acid and methacrylic acid, copolymers of vinylpyrrolidone with quaternized derivatives of dialkylaminoacrylate and -methacrylate, vinylpyrrolidone-methoimidazolinium chloride copolymers, quaternized polyvinylalcohol, polymers specified under the INCI names Polyquaternium 2, Polyquaternium 17, Polyquaternium 18, and Polyquaternium 27. Support substances in the form of water-soluble polymers in the sense of the invention are those polymers which at room temperature are soluble to an extent of more than 2.5% by weight in water.

The support substances may in accordance with the invention be used alone or else as mixtures.

According to one preferred embodiment a composition of the invention comprises, consequently, supported fragrance.

According to another preferred embodiment the composition comprising fragrance has added to it at least one substance which is known from the prior art and which extends the time period over which the period of perception of the fragrance odor of the fragrance is maintained, in comparison to the same composition without the addition of said agent prolonging the fragrance perception period, the perception period of the fragrance odor of the added fragrance being prolonged preferably by at least 10%, preferably by at least 50%, and most preferably by at least 100%.

According to a further preferred embodiment, the composition comprising fragrance has a fragrance vapor pressure at 20° C., after storage at 20° C. for 24 hours in air, of 0.0001 mbar to 5 mbar, preferably of 0.001 mbar to 2 mbar, more preferably of 0.005 mbar to 0.8 mbar and most preferably of 0.01 mbar to 0.4 mbar.

According to a further preferred embodiment the composition comprising fragrance, such as, in particular, a detergent or care product, comprises at least one, preferably two or more, active components, especially active laundering, care and/or cleaning components, advantageously selected from the group encompassing anionic surfactants, cationic surfactants, amphoteric surfactants, nonionic surfactants, acidifiers, alkalifiers, anti-crease compounds, antibacterial compounds, antioxidants, antiredeposition agents, antistats, builders, bleaches, bleach activators, bleach stabilizers, bleaching catalysts, easy-iron agents, cobuilders, fragrances, shrink preventatives, electrolytes, enzymes, color protectants, colorants, dyes, color transfer inhibitors, fluorescent agents, fungicides, germicides, odor-complexing substances, auxiliaries, hydrotropes, rinse aids, complexing agents, preservatives, corrosion inhibitors, optical brighteners, perfumes, perfume supports, pearlescence agents, pH modifiers, phobicizing and impregnating agents, polymers, swelling and anti-slip agents, foam inhibitors, phyllosilicates, soil repellents, silver protectants, silicone oils, UV protection substances, viscosity regulators, thickeners, discoloration inhibitors, graying inhibitors, vitamins and/or fabric softeners.

For the purposes of this invention, figures in % by weight for the composition of the invention refer, unless otherwise indicated, to the total weight of the composition of the invention.

The amounts of the individual ingredients in the compositions of the invention are guided in each case by the intended use of the compositions in question, and the skilled worker is familiar with the orders of magnitude of the amounts of ingredients to be used, or is able to take them from the relevant technical literature. For example, the surfactant content chosen will be higher or lower depending on the intended use of the compositions of the invention. The surfactant content of laundry detergents, for example, is typically between 10% and 50%, preferably between 12.5% and 30%, and in particular, between 15% and 25% by weight, whereas detergents for machine dishwashing typically contain between 0.1% and 10%, preferably between 0.5% and 7.5%, and in particular, between 1% and 5% by weight of surfactants.

Preferred ingredients of the compositions of the invention are described in more detail below. Anionic surfactants are preferably included in the compositions of the invention. Anionic surfactants used are, for example, those of the sulfonate and sulfate type. Useful surfactants of the sulfonate type are preferably $C_{9-13}$-alkylbenzenesulfonates, olefinsulfonates, i.e., mixtures of alkene- and hydroxyalkanesulfonates, and disulfonates, as are obtained, for example, from $C_{12-18}$-monoolefins with terminal or internal double bond by sulfonation with gaseous sulfur trioxide and subsequent alkaline or acidic hydrolysis of the sulfonation products. Also suitable are alkanesulfonates which are obtained from $C_{12-18}$-alkanes, for example by sulfochlorination or sulfoxidation with subsequent hydrolysis or neutralization. The esters of alpha-sulfo fatty acids (ester sulfonates), for example the alpha-sulfonated methyl esters of hydrogenated coconut, palm kernel or tallow fatty acids, are also likewise suitable.

Further suitable anionic surfactants are sulfated fatty acid glycerol esters. Fatty acid glycerol esters refer to the mono-, di- and triesters, and mixtures thereof, as are obtained in the preparation by esterification of a monoglycerol with from 1 to 3 mol of fatty acid or in the transesterification of triglycerides with from 0.3 to 2 mol of glycerol. Preferred sulfated fatty acid glycerol esters are the sulfation products of saturated fatty acids having from 6 to 22 carbon atoms, for example of caproic acid, caprylic acid, capric acid, myristic acid, lauric acid, palmitic acid, stearic acid or behenic acid.

Preferred alk(en)yl sulfates are the alkali metal and in particular, the sodium salts of the sulfuric monoesters of $C_{12}$-$C_{18}$ fatty alcohols, for example of coconut fatty alcohol, tallow fatty alcohol, lauryl, myristyl, cetyl or stearyl alcohol, or of $C_{10}$-$C_{20}$ oxo alcohols and those monoesters of secondary alcohols of these chain lengths. Also preferred are alk(en)yl sulfates of the chain length mentioned which contain a synthetic straight-chain alkyl radical prepared on a petrochemical basis and which have analogous degradation behavior to the equivalent compounds based on fatty chemical raw materials. From the washing point of view, preference is given to the $C_{12}$-$C_{16}$-alkyl sulfates and $C_{12}$-$C_{15}$-alkyl sulfates, and $C_{14}$-$C_{15}$-alkyl sulfates. 2,3-Alkyl sulfates, obtainable as commercial products from the Shell Oil Company under the name DAN®, are also suitable anionic surfactants.

Also suitable are the sulfuric monoesters of the straight-chain or branched $C_{7-21}$-alcohols ethoxylated with 1 to 6 mol of ethylene oxide, such as 2-methyl-branched $C_{9-11}$-alcohols with on average 3.5 mol of ethylene oxide (EO) or $C_{12-18}$-fatty alcohols with from 1 to 4 EO. Owing to their high tendency to foam, they are used in cleaning compositions only in relatively small amounts, for example amounts of from 1 to 5% by weight.

A further class of anionic surfactants is the class of ethercarboxylic acids obtainable by reaction of fatty alcohol ethoxylates with sodium chloroacetate in the presence of basic catalysts. They have the general formula: $R^{10}O—(CH_2—CH_2—O)_p—CH_2—COOH$ where $R^{10}$=$C_1$-$C_{18}$ and p=from 0.1 to 20. Ethercarboxylic acids are water hardness-insensitive and have outstanding surfactant properties. Preparation and use are described, for example, in Seifen, Öle, Fette, Wachse 101, 37 (1975); 115, 235 (1989) and Tenside Deterg. 25, 308 (1988).

Suitable anionic surfactants are, for example, also the partial esters of di- or polyhydroxyalkanes, mono- and disaccharides, polyethylene glycols with the ene adducts of maleic anhydride to at least monounsaturated carboxylic acids having a chain length of from 10 to 25 carbon atoms, with an acid number of from 10 to 140, which are described in German Patent No. DE 38 08 114 A1 (Grillo-Werke) and in European Patent No. EP 0 046 070 A (Grillo-Werke), to which reference is made in this regard and the contents of both are hereby incorporated into this application.

Preferred anionic surfactants have not only an unbranched or branched, saturated or unsaturated, aliphatic or aromatic, acyclic or cyclic, optionally alkoxylated alkyl radical having from 4 to 28, preferably from 6 to 20, in particular, from 8 to 18, more preferably from 10 to 16, exceptionally preferably from 12 to 14, carbon atoms, but also two or more anionic, in particular, two, acid groups, preferably carboxylate, sulfonate and/or sulfate groups, in particular, one carboxylate and one sulfate group. Examples of these compounds are the alpha-sulfo fatty acid salts, the acyl glutamates, the monoglyceride disulfates and the alkyl ethers of glyceryl disulfate, and in particular, the monoesterified sulfosuccinates described below.

Particularly preferred anionic surfactants are the sulfosuccinates, sulfosuccinamates and sulfosuccinamides, in particular, sulfosuccinates and sulfosuccinamates, exceptionally preferably sulfosuccinates. The sulfosuccinates are the salts of the mono- and diesters of sulfosuccinic acid HOOCCH($SO_3H$)$CH_2COOH$, while the sulfosuccinamates refer to the salts of monoamides of sulfosuccinic acid and the sulfosuccinamides to the salts of diamides of sulfosuccinic acid. A comprehensive description of these known anionic surfactants is provided by A. Domsch and B. Irrgang in Anionic surfactants: organic chemistry (edited by H. W. Stache; Surfactant science series; volume 56; ISBN 0-8247-9394-3; Marcel Dekker, Inc., New York 1996, pp. 501-549).

The salts are preferably alkali metal salts, ammonium salts and also mono-, di- and trialkanolammonium salts, for example mono-, di- and triethanolammonium salts, in particular, lithium, sodium, potassium or ammonium salts, more preferably sodium or ammonium salts, exceptionally preferably sodium salts.

In the sulfosuccinates, one or both carboxyl groups of sulfosuccinic acid has/have preferably been esterified with one or two identical or different, unbranched or branched, saturated or unsaturated, acyclic or cyclic, optionally alkoxylated alcohols having from 4 to 22, preferably from 6 to 20, in particular, from 8 to 18, more preferably from 10 to 16, exceptionally preferably from 12 to 14, carbon atoms. Particular preference is given to the esters of unbranched and/or saturated and/or acyclic and/or alkoxylated alcohols, in particular, unbranched, saturated fatty alcohols and/or unbranched, saturated fatty alcohols alkoxylated with ethylene oxide and/or propylene oxide, preferably ethylene oxide, and having a degree of alkoxylation of from 1 to 20, preferably from 1 to 15, in particular, from 1 to 10, more preferably from 1 to 6, exceptionally preferably from 1 to 4. In the context of the present invention, the monoesters are preferred over the diesters. A particularly preferred sulfosuccinate is sulfosuccinic acid lauryl polyglycol ester disodium salt (lauryl-EO sulfosuccinate, disodium salt; INCI Disodium Laureth Sulfosuccinate), which is commercially available, for example, as Tego® Sulfosuccinat F 30 (Goldschmidt) having a sulfosuccinate content of 30% by weight.

In the sulfosuccinamates or sulfosuccinamides, one or both carboxyl groups of sulfosuccinic acid preferably form(s) a carboxamide with a primary or secondary amine which bears one or two identical or different, unbranched or branched, saturated or unsaturated, acyclic or cyclic, optionally alkoxylated alkyl radicals having from 4 to 22, preferably from 6 to 20, in particular, from 8 to 18, more preferably from 10 to 16, exceptionally preferably from 12 to 14, carbon atoms. Particular preference is given to unbranched and/or saturated and/or acyclic alkyl radicals, in particular, unbranched, saturated fatty alkyl radicals.

Also suitable are, for example, the following sulfosuccinates and sulfosuccinamates designated according to INCI, which are described in detail in the International Cosmetic Ingredient Dictionary and Handbook: Ammonium Dinonyl Sulfosuccinate, Ammonium Lauryl Sulfosuccinate, Diammonium Dimethicone Copolyol Sulfosuccinate, Diammonium Lauramido-MEA Sulfosuccinate, Diammonium Lauryl Sulfosuccinate, Diammonium Oleamido PEG-2 Sulfosuccinate, Diamyl Sodium Sulfosuccinate, Dicapryl Sodium Sulfosuccinate, Dicyclohexyl Sodium Sulfosuccinate, Diheptyl Sodium Sulfosuccinate, Dihexyl Sodium Sulfosuccinate, Diisobutyl Sodium Sulfosuccinate, Dioctyl Sodium Sulfosuccinate, Disodium Cetearyl Sulfosuccinate, Disodium Cocamido MEA-Sulfosuccinate, Disodium Cocamido Glucoside Sulfosuccinate, Disodium Cocoyl Butyl Gluceth-10 Sulfosuccinate, Disodium C12-15 Pareth Sulfosuccinate, Disodium Deceth-5 Sulfosuccinate, Disodium Deceth-6 Sulfosuccinate, Disodium Dihydroxyethyl Sulfosuccinylundecylenate, Disodium Dimethicone Copolyol Sulfosuccinate, Disodium Hydrogenated Cottonseed Glyceride Sulfosuccinate, Disodium Isodecyl Sulfosuccinate, Disodium Isostearamido MEA-Sulfosuccinate, Disodium Isostearamido MIPA-Sulfosuccinate, Disodium Isostearyl Sulfosuccinate, Disodium Laneth-5 Sulfosuccinate, Disodium Lauramido MEA-Sulfosuccinate, Disodium Lauramido PEG-2 Sulfosuccinate, Disodium Lauramido PEG-5 Sulfosuccinate, Disodium Laureth-6 Sulfosuccinate, Disodium Laureth-9 Sulfosuccinate, Disodium Laureth-12 Sulfosuccinate, Disodium Lauryl Sulfosuccinate, Disodium Myristamido MEA-Sulfosuccinate, Disodium Nonoxynol-10 Sulfosuccinate, Disodium Oleamido MEA-Sulfosuccinate, Disodium Oleamido MIPA-Sulfosuccinate, Disodium Oleamido PEG-2 Sulfosuccinate, Disodium Oleth-3 Sulfosuccinate, Disodium Oleyl Sulfosuccinate, Disodium Palmitamido PEG-2 Sulfosuccinate, Disodium Palmitoleamido PEG-2 Sulfosuccinate, Disodium PEG-4 Cocamido MIPA-Sulfosuccinate, Disodium PEG-5 Laurylcitrate Sulfosuccinate, Disodium PEG-8 Palm Glycerides Sulfosuccinate, Disodium Ricinoleamido MEA-Sulfosuccinate, Disodium Sitostereth-14 Sulfosuccinate, Disodium Stearamido MEA-Sulfosuccinate, Disodium Stearyl Sulfosuccinamate, Disodium Stearyl Sulfosuccinate, Disodium Tallamido MEA-Sulfosuccinate, Disodium Tallowamido MEA-Sulfosuccinate, Disodium Tallow Sulfosuccinamate, Disodium Tridecylsulfosuccinate, Disodium Undecylenamido MEA-Sulfosuccinate, Disodium Undecylenamido PEG-2 Sulfosuccinate, Disodium Wheat Germamido MEA-Sulfosuccinate, Disodium Wheat Germamido PEG-2 Sulfosuccinate, Di-TEA-Oleamido PEG-2 Sulfosuccinate, Ditridecyl Sodium Sulfosuccinate, Sodium Bisglycol Ricinosulfosuccinate, Sodium/MEA Laureth-2 Sulfosuccinate and Tetrasodium Dicarboxyethyl Stearyl Sulfosuccinamate. Yet another suitable sulfosuccinamate is disodium $C_{16-18}$-alkoxypropylene sulfosuccinamate.

The amount of anionic surfactants, preferably of the stated anionic surfactants, in the composition of the invention may vary within wide ranges, according to the purpose served by the composition in question. Thus, a composition of the invention may contain very large amounts of anionic surfactant, preferably up to an order of magnitude of 50% by weight or more. A composition of the invention may likewise contain only very small amounts of anionic surfactants, such as less than 10% by weight or less than 5% by weight or even less, for example. In the compositions of the invention, however, there are advantageously anionic surfactants in amounts of 2% to 30% and in particular, 5% to 25% by weight, particular preference being given to concentrations above 10% by weight and even above 15% by weight.

In addition to the stated anionic surfactants, but also independently of them, it is possible for there to be soaps in the compositions of the invention. Particularly suitable are saturated fatty acid soaps, such as the salts of lauric acid, myristic acid, palmitic acid, stearic acid, hydrogenated erucic acid, and behenic acid, and also, in particular, soap mixtures derived from natural fatty acids, e.g., coconut, palm kernel or tallow fatty acids. The amount of soaps in the composition, independently of other anionic surfactants, is preferably not more than 3% by weight, and in particular, 0.5% to 2.5% by weight.

The anionic surfactants and soaps can be in the form of their sodium, potassium or ammonium salts and also as soluble salts of organic bases, such as mono-, di- or triethanolamine. Preferably they are in the form of their sodium or potassium salts, especially in the form of the sodium salts. Anionic surfactants and soaps can also be prepared in situ, by incorporating the anionic surfactant acids and, where appropriate, fatty acids into the composition for spray drying, these acids then being neutralized by the alkali carriers in the composition for spray drying.

Advantageously it is possible for nonionic surfactants, likewise, to be present in the compositions of the invention, both in solid and in liquid compositions. When the solid compositions are directly spray-dried compositions of the invention, then nonionic surfactants are present preferably only in minor amounts. By way of example their amount in directly spray-dried compositions of the invention of this kind can amount to up to 2% or 3% by weight. When the compositions of the invention are not directly spray-dried compositions, it is also possible for greater amounts of nonionic surfactant to be present, such as, for example, around 5% or 10% or 15% or 20% or 30% by weight or even more, if appropriate.

Preferably, however, the nonionic surfactants are included in amounts up to 50%, advantageously from 0.1% to 40%, more preferably from 0.5% to 30%, and in particular, from 2% to 25%, by weight, based in each case on the overall composition.

It is possible advantageously for all of the nonionic surfactants known from the prior art to be present in the compositions of the invention. For a precise description of the nonionic surfactants, reference is made to the description of what are called the after-treated products further on below. All of the nonionic surfactants described there may be present advantageously in the compositions of the invention.

After-treated products are solid products which are produced initially by customary methods, such as by granulation or compounding, in particular, by spray drying, and are then subjected to a further treatment, the after treatment. For example it is possible for a product obtained directly by spray drying to be subsequently after-treated with nonionic surfactants.

The compositions of the invention, such as, in particular, detergents and care compositions, may preferably also contain cationic surfactants. Examples of suitable cationic surfactants are surface-active quaternary compounds, having in particular, an ammonium, sulfonium, phosphonium, iodonium or arsonium group as described by K. H. Wallhäußer in "Prascis der Sterilisation, Desinfektion—Konservierung: Keimidentifizierung—Betriebshygiene" (5th ed.—Stuttgart; New York: Thieme, 1995) as antimicrobial active substances. Through the use of quaternary surface-active compounds with antimicrobial action it is possible to design the composition with an antimicrobial action or to enhance its antimicrobial action where such action is already present, where appropriate, on the basis of other ingredients.

Particularly preferred cationic surfactants are quaternary, in some cases antimicrobially active ammonium compounds (QACs; INCI Quaternary Ammonium Compounds) of the general formula $(R^{I})(R^{II})(R^{III})(R^{IV})N^{+}X^{-}$ in which $R^{I}$ to $R^{IV}$ are identical or different $C_{1-22}$-alkyl radicals, $C_{7-28}$-aralkyl radicals or heterocyclic radicals, in which two, or, in the case of an aromatic incorporation as in pyridine, even three radicals, together with the nitrogen atom form the heterocycle, for example a pyridinium or imidazolinium compound, and $X^{-}$ are halide ions, sulfate ions, hydroxide ions or similar anions. For an optimum antimicrobial action, at least one of the radicals preferably has a chain length of from 8 to 18, in particular, from 12 to 16, carbon atoms.

QACs can be prepared by reacting tertiary amines with alkylating agents, for example methyl chloride, benzyl chloride, dimethyl sulfate, dodecyl bromide, but also ethylene oxide. The alkylation of tertiary amines having a long alkyl radical and two methyl groups succeeds particularly readily, and the quaternization of tertiary amines having two long radicals and a methyl group may also be carried out with the aid of methyl chloride under mild conditions. Amines which have three long alkyl radicals or hydroxyl-substituted alkyl radicals have low reactivity and are preferably quaternized with dimethyl sulfate.

Suitable QACs are, for example, benzalkonium chloride (N-alkyl-N,N-dimethylbenzylammonium chloride, CAS No. 8001-54-5), benzalkone B (m,p-dichlorobenzyldimethyl-$C_{1-2}$-alkylammonium chloride, CAS No. 58390-78-6), benzoxonium chloride (benzyldodecylbis(2-hydroxyethyl)ammonium chloride), cetrimonium bromide (N-hexadecyl-N,N-trimethylammonium bromide, CAS No. 57-09-0), benzetonium chloride (N,N-dimethyl-N-[2-[2-[p-(1,1,3,3-tetramethylbutyl)phenoxy]ethoxy]ethyl]benzylammonium chloride, CAS No. 121-54-0), dialkyldimethylammonium chlorides such as di-n-decyldimethylammonium chloride (CAS No. 7173-51-5-5), didecyldimethylammonium bromide (CAS No. 2390-68-3), dioctyldimethylammonium chloride, 1-cetylpyridinium chloride (CAS No. 123-03-5) and thiazoline iodide (CAS No. 15764-48-1) and also mixtures thereof. Preferred QACs are the benzalkonium chlorides having $C_8$-$C_{18}$-alkyl radicals, in particular, $C_{12}$-$C_{14}$-alkylbenzyldimethylammonium chloride. A particularly preferred QAC is cocopentaethoxymethylammonium methosulfate (INCI PEG-5 Cocomonium Methosulfate; Rewoquat® CPEM).

To avoid possible incompatibilities of the antimicrobial cationic surfactants with the anionic surfactants present in the composition of the invention, very substantially anionic-surfactant-compatible and/or very little cationic surfactant is used, or, in a preferred embodiment of the invention, cationic surfactants are dispensed with entirely.

Later on below, particularly in connection with conditioners and softeners, a description is given of further cationic surfactants, including quaternary ammonium compounds. These two may preferably be present in the compositions of the invention.

The compositions of the invention, such as preferably detergents and care products, may comprise one or more cationic surfactants, advantageously in amounts, based on the overall constitution, of 0% to 30%, more advantageously greater than 0% to 20%, preferably 0.01% to 10%, and in particular, 0.1% to 5% by weight.

The compositions of the invention, such as preferably detergents and care products, may also comprise amphoteric surfactants. These surfactants too are described in more detail later on below, particularly in connection with conditioners and softeners.

The compositions of the invention, such as detergents and care products, may comprise one or more amphoteric surfactants, advantageously in amounts, based on the overall constitution, of 0% to 30%, more advantageously greater than 0% to 20%, preferably 0.01% to 10%, in particular, 0.1% to 5%, by weight.

Further ingredients of the compositions of the invention may be organic and inorganic builder substances. The inorganic builder substances include water-insoluble or non-water-soluble ingredients, such as aluminosilicates and, in particular, zeolites. In one preferred embodiment the composition of the invention contains no phosphate and/or no zeolite.

It is, however, also possible for the composition to contain zeolite, in which case it is preferred for this zeolite fraction, based on the overall weight of the composition, to be less than 5%, preferably not more than 4%, not more than 3%, or not more than 2%, by weight.

The composition of the invention may, however, also advantageously be envisaged as having a zeolite content of at least 10% by weight, e.g., at least 15% or at least 20% by weight, or even more, at least 50% by weight for example.

Soluble builders can be present in the composition of the invention preferably in amounts of 10% to 30% by weight, preferably 15% to 25% by weight, and more preferably 18% to 20% by weight, based on the total weight of the composition, with sodium carbonate being a particularly preferred soluble builder. It is also possible, advantageously, to envisage the composition of the invention containing less than 10% by weight, less than 5% by weight for example, of soluble builder.

Useful finely crystalline, synthetic zeolite, containing bound water, is preferably zeolite A and/or P. A particularly preferred zeolite P is, for example, Zeolite MAP® (commercial product from Crosfield). Also suitable, however, are zeolite X and also mixtures of A, X and/or P. Also of particular interest is a cocrystallized sodium/potassium aluminum silicate of zeolite A and zeolite X, which is available commercially as VEGOBOND AX® (commercial product from Condea Augusta S.p.A.). This product is described in more detail below. The zeolite can be employed as a spray dried powder or else as an undried, stabilized suspension still wet from its preparation. Where the zeolite is used as suspension it is possible for said suspension to include small additions of nonionic surfactants as stabilizers: for example, from 1 to 3% by weight, based on zeolite, of ethoxylated $C_{12}$-$C_{18}$ fatty alcohols having 2 to 5 ethylene oxide groups, $C_{12}$-$C_{14}$ fatty alcohols having 4 to 5 ethylene oxide groups or ethoxylated isotridecanols. Suitable zeolites have an average particle size of preferably less than 10 μm (volume distribution; measurement method: Coulter counter) and contain preferably from 18 to 22% by weight, in particular, from 20 to 22% by weight, of bound water.

Further particularly suitable zeolites include zeolites of the faujasite type. Together with zeolites X and Y, the mineral faujasite is one of the faujasite types within zeolite structural group 4 which are characterized by the double six-membered ring subunit D6R (compare Donald W. Breck: "Zeolite Molecular Sieves," John Wiley & Sons, New York, London, Sydney, Toronto, 1974, page 92). In addition to said faujasite types, zeolite structural group 4 includes the mineral chabazite and gmelinite and also the synthetic zeolites R (chabazite type), S (gmelinite type), L, and ZK-5. The two last-mentioned synthetic zeolites have no mineral analogs.

Zeolites of the faujasite type are composed of β cages linked tetrahedrally via D6R subunits, the β cages being arranged similarly to the carbon atoms in a diamond. The three-dimensional network of the faujasite-type zeolites suitable in accordance with the invention has pores of 2.2 and 7.4 Å; the unit cell further contains 8 cavities of approximately 13 Å in diameter and may be described by the formula $Na_{86}[(AlO_2)_{86}(SiO_2)_{106}].264H_2O$. The network of zeolite X contains a cavity volume of approximately 50%, based on the dehydrated crystal, which represents the greatest empty space of all known zeolites (zeolite Y: approximately 48% cavity volume; faujasite: approximately 47% cavity volume). (All data from: Donald W. Breck: "Zeolite Molecular Sieves," John Wiley & Sons, New York, London, Sydney, Toronto, 1974, pages 145, 176, 177.)

In the context of the present invention, the term "faujasite-type zeolite" characterizes all three zeolites which form the faujasite subgroup of zeolite structural group 4. In accordance with the invention, therefore, not only zeolite X but also zeolite Y and faujasite, and mixtures of these compounds, are suitable, preference being given to straight zeolite X.

Also suitable in accordance with the invention are mixtures or cocrystallizates of faujasite-type zeolites with other zeolites, which need not necessarily belong to zeolite structural group 4, with preferably at least 50% by weight of the zeolites being faujasite-type zeolites.

The suitable aluminum silicates are available commercially and the methods of preparing them are described in standard monographs.

Examples of commercially available zeolites of the X type may be described by the following formulas:

$$Na_{86}[(AlO_2)_{86}(SiO_2)_{106}].xH_2O$$

$$K_{86}[(AlO_2)_{86}(SiO_2)_{106}].xH_2O$$

$$Ca_{40}Na_6[(AlO_2)_{86}(SiO_2)_{106}].xH_2O$$

$$Sr_{21}Ba_{22}[AlO_2)_{86}(SiO_2)_{106}].xH_2O$$

where x may adopt values between 0 and 276. These zeolites have pore sizes of from 8.0 to 8.4 Å.

Also suitable, for example, is zeolite A-LSX described in European patent application EP-A-816 291, which corresponds to a cocrystallizate of zeolite X and zeolite A and in its anhydrous form possesses the formula $(M_{2/n}O+M'_{2/n}O).Al_2O_3.zSiO_2$, where M and M' can be alkali metals or alkaline earth metals and z is a number between 2.1 and 2.6. This product is available commercially under the brand name VEGOBOND AX from CONDEA Augusta S.p.A.

Zeolites of the Y type are also available commercially and may be described, for example, by the formulas $$Na_{56}[(AlO_2)_{56}(SiO_2)_{136}].xH_2O$$

$$K_{56}[(AlO_2)_{56}(SiO_2)_{136}].xH_2O$$

where x is numbers greater than 0 up to 276. These zeolites have pore sizes of 8.0 Å.

The particle sizes of the suitable zeolites is advantageously in the range from 0.1 μm up to 100 μm, preferably from 0.5 μm up to 50 μm, and in particular, from 1 μm up to 30 μm, in each case measured by standard particle size determination methods.

In one preferred embodiment of the invention all of the inorganic constituents present are to be preferably water-soluble. In these embodiments, therefore, builder substances other than the zeolites already mentioned are used.

Further suitable builder substances are polyacetals, which can be obtained by reacting dialdehydes with polyolcarboxylic acids containing 5 to 7 carbon atoms and at least 3 hydroxyl groups, as described for example, in European Patent Application No. EP-A-0 280 223. Preferred polyacetals are obtained from dialdehydes such as glyoxal, glutaraldehyde, terephthalaldehyde, and mixtures thereof, and from polyolcarboxylic acids such as gluconic acid and/or glucoheptonic acid.

Further suitable organic builder substances are dextrins, examples being oligomers or polymers of carbohydrates which are obtainable by partial hydrolysis of starches. The hydrolysis may be carried out by typical methods, examples being acid- or enzyme-catalyzed methods. The hydrolysis products in question are preferably those having average molar masses in the range from 400 to 500,000 g/mol. Preference is given here to a polysaccharide having a dextrose equivalent (DE) in the range from 0.5 to 40, in particular, from 2 to 30, DE being a customary measure of the reducing effect of a polysaccharide in comparison to dextrose, which possesses a DE of 100. It is possible to use not only maltodextrins with a DE between 3 and 20 and dry glucose syrups with a DE between 20 and 37 but also so-called yellow dextrins and white dextrins with higher molar masses in the range from 2,000 to 30,000 g/mol. A preferred dextrin is described in British Patent Application No. 94 19 091. The oxidized derivatives of such dextrins are their reaction products with oxidizing agents which are capable of oxidizing at least one alcohol function of the saccharide ring to the carboxylic acid function. Oxidized dextrins of this kind and methods for their preparation are known, for example from European Patent Application Nos. EP-A-0 232 202, EP-A-0 427 349, EP-A-0 472 042 and EP-A-0 542 496 as well as from International Patent Application Nos. WO 92/18542, WO-A-93/08251, WO-A-93/16110, WO-A-94(28030, WO-A-95/07303, WO-A-95/12619 and WO-A-95/20608. Likewise suitable is an oxidized oligosaccharide according to German Patent Application No. DE-A-196 00 018. A product oxidized at $C_6$ of the saccharide ring may be particularly advantageous.

Oxydisuccinates and other derivatives of disuccinates as well, preferably ethylenediaminedisuccinate, are further suitable cobuilders. Ethylenediamine-N,N'-disuccinate (EDDS), whose synthesis is described for example in U.S. Pat. No. 3,158,615, is used preferably in the form of its sodium or magnesium salts. Preference is additionally given in this context to glycerol disuccinates and glycerol trisuccinates, of the kind described for example in U.S. Pat. Nos. 4,524,009 and 4,639,325, in European Patent Application No. EP-A-0 150 930 and Japanese Patent Application JP 93/339896. Suitable amounts for use are 3% to 15% by weight, based on the composition as a whole.

Further useful organic cobuilders are, for example, acetylated hydroxycarboxylic acids and their salts, which where appropriate may also be present in lactone form and which contain at least 4 carbon atoms and at least one hydroxyl group and also not more than two acid groups. Cobuilders of this kind are described, for example, in International Patent Application No. WO-A-95/20029.

A further class of substance having cobuilder properties is represented by the phosphonates. These are, in particular, hydroxyalkanephosphonates and aminoalkanephosphonates. Among the hydroxyalkanephosphonates, 1-hydroxyethane-1,1-diphosphonate (HEDP) is of particular importance as a cobuilder. It is used preferably as the sodium salt, the disodium salt giving a neutral reaction and the tetrasodium salt an alkaline (pH 9) reaction. Suitable aminoalkanephosphonates include, preferably, ethylenediaminetetramethylenephosphonate (EDTMP), diethylenetriaminepentamethylenephosphonate (DTPMP), and their higher homologues. They are used preferably in the form of the neutrally reacting sodium salts, e.g., as the hexasodium salt of EDTMP and as the heptasodium and octasodium salts of DTPMP. Builders used in this case, from the class of the phosphonates, are preferably HEDP. The aminoalkanephosphonates possess, furthermore, a pronounced heavy metal-binding capacity. Accordingly, particularly if the compositions also contain bleach, it can be preferable to use aminoalkanephosphonates, especially DTPMP, or mixtures of the stated phosphonates.

In cases where a phosphate content is tolerated it is also possible to use phosphates, especially pentasodium triphosphate, and possibly also pyrophosphates, and orthophosphates, which act primarily as precipitants for lime salts. Phosphates are used predominantly in machine dishwashing detergents but in some cases also in laundry detergents as well. Alkali metal phosphates is the collective term for the alkali metal (especially sodium and potassium) salts of the various phosphoric acids, among which metaphosphoric acids $(HPO_3)_n$ and orthophosphoric acid $H_3PO_4$, in addition to higher-molecular-mass representatives, may be distinguished. The phosphates combine a number of advantages: they act as alkali carriers, prevent limescale deposits on machine components, and lime incrustations in fabrics, and additionally contribute to cleaning performance.

Sodium dihydrogen phosphate, $NaH_2PO_4$, exists as the dihydrate (density 1.91 g $cm^{-3}$, melting point 60°) and as the monohydrate (density 2.04 g $cm^{-3}$). Both salts are white powders of very ready solubility in water which lose the water of crystallization on heating and undergo conversion at 200° C. into the weakly acidic diphosphate (disodium hydrogen diphosphate, $Na_2H_2P_2O_7$) and at the higher temperature into sodium trimetaphosphate ($Na_3P_3O_9$) and Maddrell's salt (see below). $NaH_2PO_4$ reacts acidically; it is formed if phosphoric acid is adjusted to a pH of 4.5 using sodium hydroxide solution and the slurry is sprayed. Potassium dihydrogen phosphate (primary or monobasic potassium phosphate, potassium biphosphate, PDP), $KH_2PO_4$, is a white salt with a density of 2.33 g $cm^{-3}$, has a melting point of 253° [decomposition with formation of potassium polyphosphate $(KPO_3)_x$], and is readily soluble in water.

Disodium hydrogen phosphate (secondary sodium phosphate), $Na_2HPO_4$, is a colorless, crystalline salt which is very readily soluble in water. It exists in anhydrous form and with 2 mol (density 2.066 g $cm^{-3}$, water loss at 95°), 7 mol (density 1.68 g $cm^{-3}$, melting point 48° with loss of $5H_2O$), and 12 mol of water (density 1.52 g $cm^{-3}$, melting point 35° with loss of $5H_2O$), becomes anhydrous at 100°, and if heated more severely undergoes transition to the diphosphate $Na_4P_2O_7$. Disodium hydrogen phosphate is prepared by neutralizing phosphoric acid with sodium carbonate solution using phenolphthalein as indicator. Dipotassium hydrogen phosphate (secondary or dibasic potassium phosphate), $K_2HPO_4$, is an amorphous white salt which is readily soluble in water.

Trisodium phosphate, tertiary sodium phosphate, $Na_3PO_4$, are colorless crystals which as the dodecahydrate have a density of 1.62 g $cm^{-3}$ and a melting point of 73-76° C. (decomposition), as the decahydrate (corresponding to 19-20% $P_2O_5$) have a melting point of 100° C., and in anhydrous form (corresponding to 39-40% $P_2O_5$) have a density of 2.536 g $cm^{-3}$. Trisodium phosphate is readily soluble in water, with an alkaline reaction, and is prepared by evaporative concentration of a solution of precisely 1 mol of disodium phosphate and 1 mol of NaOH. Tripotassium phosphate (tertiary or tribasic potassium phosphate), $K_3PO_4$, is a white, deliquescent, granular powder of density 2.56 g $cm^{-3}$, has a melting point of 1340°, and is readily soluble in water with an alkaline reaction. It is produced, for example, when Thomas slag is heated with charcoal and potassium sulfate. Despite the relatively high price, the more readily soluble and therefore highly active potassium phosphates are frequently preferred in the cleaning products industry over corresponding sodium compounds.

Tetrasodium diphosphate (sodium pyrophosphate), $Na_4P_2O_7$, exists in anhydrous form (density 2.534 g $cm^{-3}$, melting point 988°, 880° also reported) and as the decahydrate (density 1.815-1.836 g $cm^{-3}$, melting point 94° with loss of water). Both substances are colorless crystals which dissolve in water with an alkaline reaction. $Na_4P_2O_7$ is formed when disodium phosphate is heated at >200° or by reacting phosphoric acid with sodium carbonate in stoichiometric ratio and dewatering the solution by spraying. The decahydrate complexes heavy metal salts and water hardeners and therefore reduces the hardness of the water. Potassium diphosphate (potassium pyrophosphate), $K_4P_2O_7$, exists in the form of the trihydrate and is a colorless, hygroscopic powder of density 2.33 g $cm^{-3}$ which is soluble in water, the pH of the 1% strength solution at 25° being 10.4.

Condensation of $NaH_2PO_4$ or of $KH_2PO_4$ gives rise to higher-molecular-mass sodium and potassium phosphates, among which it is possible to distinguish cyclic representatives, the sodium and potassium metaphos-phates, and catenated types, the sodium and potassium polyphosphates. For the latter in particular, a large number of names are in use: fused or calcined phosphates, Graham's salt, Kurrol's and Maddrell's salt. All higher sodium and potassium phosphates are referred to collectively as condensed phosphates.

The industrially important pentasodium triphosphate, $Na_5P_3O_{10}$ (sodium tripolyphosphate), is a nonhygroscopic, white, water-soluble salt which is anhydrous or crystallizes with $6H_2O$ and has the general formula NaO—[P(O)(ONa)—O]$_n$—Na where n=3. About 17 g of the anhydrous salt dissolve in 100 g of water at room temperature, at 60° about 20 g, at 100° around 32 g; after heating the solution at 100° C. for two hours, about 8% orthophosphate and 15% diphosphate are produced by hydrolysis. For the preparation of pentasodium triphosphate, phosphoric acid is reacted with sodium carbonate solution or sodium hydroxide solution in stoichiometric ratio and the solution is dewatered by spraying. In a similar way to Graham's salt and sodium diphosphate, pentasodium triphosphate dissolves numerous insoluble metal compounds (including lime soaps, etc). Pentapotassium triphosphate, $K_5P_3O_{10}$ (potassium tripolyphosphate), is commercialized, for example, in the form of a 50% strength by weight solution (>23% $P_2O_5$, 25% $K_2O$). The potassium polyphosphates find broad application in the laundry detergents and cleaning products industry. There also exist sodium potassium tripolyphosphates, which may likewise be used for the purposes of the present invention. These are formed, for example, when sodium trimetaphosphate is hydrolyzed with KOH:

$$(NaPO_3)_3+2KOH \rightarrow Na_3K_2P_3O_{10}+H_2O$$

They can be used in accordance with the invention in precisely the same way as sodium tripolyphosphate, potassium tripolyphosphate, or mixtures of these two; mixtures of sodium tripolyphosphate and sodium potassium tripolyphosphate, or mixtures of potassium tripolyphosphate and sodium potassium tripolyphosphate, or mixtures of sodium tripolyphosphate and potassium tripolyphosphate and sodium potassium tripolyphosphate, may also be used in accordance with the invention.

In one preferred embodiment of the invention, however, carbonates and silicates are used in particular, as inorganic builder substances.

Mention should be made here in particular, of crystalline, layered sodium silicates possessing the general formula $NaMSi_xO_{2x+1}.yH_2O$, where M is sodium or hydrogen, x is a number from 1.6 to 4, preferably from 1.9 to 4, y is a number from 0 to 20, and preferred values for x are 2, 3 or 4. Since, however, crystalline silicates of this kind lose their crystalline structure, at least partly, in a spray drying process, crystalline silicates are preferably admixed subsequently to the direct or after-treated spray drying product. Crystalline phyllosilicates of this kind are described, for example, in European Patent Application No. EP-A-0 164 514. Preferred crystalline phyllosilicates of the formula indicated are those in which M is sodium and x adopts the value 2 or 3. In particular, both β- and δ-sodium disilicates $Na_2Si_2O_5.yH_2O$ are preferred. Compounds of this kind are in commerce, for example, under the designation SKS® (Clariant). Thus in the case of SKS-6® the product is predominantly a δ-sodium disilicate with the formula $Na_2Si_2O_5.yH_2O$; SKS-7® is predominantly the β-sodium disilicate. Reaction with acids (e.g., citric acid or carbonic acid) produces from the δ-sodium disilicate kanemite $NaHSi_2O_5.yH_2O$, in commerce under the designations SKS-9® and SKS-10® (Clariant), respectively. It may also be of advantage to use chemical modifications of these phyllosilicates. For example, the alkalinity of the phyllosilicates can be influenced appropriately. As compared with δ-sodium disilicate, phosphate-doped and/or carbonate-doped phyllosilicates have altered crystal morphologies, dissolve more rapidly, and exhibit a calcium-binding power which is higher than that of δ-sodium disilicate. Thus phyllosilicates of the general empirical formula $xNa_2O.ySiO_2.z P_2O_5$, in which the ratio of x to y corresponds to a number from 0.35 to 0.6, the ratio of x to z corresponds to a number from 1.75 to 1200, and the ratio of y to z corresponds to a number of from 4 to 2,800, are described in the patent application DE-A-196 01 063. The solubility of the phyllosilicates can also be increased, by using particularly finely divided phyllosilicates. Compounds of the crystalline phyllosilicates with other ingredients can be used as well. Mention may be made in particular, in this context of compounds with cellulose derivatives, which have advantages in the disintegrating effect, and compounds with polycarboxylates, e.g., citric acid, and/or polymeric polycarboxylates, e.g., copolymers of acrylic acid.

The preferred builder substances also include amorphous sodium silicates having an $Na_2O:SiO_2$ modulus of from 1:2 to 1:3.3, preferably from 1:2 to 1:2.8, and in particular, from 1:2 to 1:2.6, which have secondary washing properties. In the context of this invention, the term "amorphous" also embraces "X-ray-amorphous." This means that in X-ray diffraction experiments the silicates do not yield the sharp X-ray reflections typical of crystalline substances but instead yield at best one or more maxima of the scattered X-radiation, having a width of several degree units of the diffraction angle. However, good builder properties may result, very probably even particularly good builder properties, if the silicate particles in electron diffraction experiments yield vague or even sharp diffraction maxima. The interpretation of this is that the products have microcrystalline regions with a size of from 10 to several hundred nm, values up to maximum 50 nm and in particular, up to maximum 20 nm being preferred. So-called X-ray-amorphous silicates of this kind, which likewise possess retarded dissolution relative to the conventional waterglasses, are described, for example, in German Patent Application No. DE-A-44 00 024. Particular preference is given to compressed compacted amorphous silicates, compounded amorphous silicates, and overdried X-ray-amorphous silicates. The amount of the (X-ray-)amorphous silicates particularly in zeolite-free compositions is preferably 1% to 10% by weight, which corresponds to one preferred embodiment of the invention.

Particularly preferred inorganic water-soluble builders, however, are alkali metal carbonates and alkali metal bicarbonates, with the preferred embodiments including sodium and potassium carbonate and, in particular, sodium carbonate. The amount of the alkali metal carbonates in particularly zeolite-free compositions can vary within a very broad spectrum and is preferably from 5 to 40% by weight, in particular, from 8 to 30% by weight, with the amount of alkali metal carbonates usually being higher than that of (X-ray-amorphous silicates.

Organic builder substances which may be used are, for example, the polycarboxylic acids, usable in the form of their alkali metal and especially sodium salts, such as citric acid, adipic acid, succinic acid, glutaric acid, tartaric acid, sugar acids, amino carboxylic acids, nitrilotriacetic acid (NTA), provided such use is not objectionable on ecological grounds, and also mixtures thereof. Preferred salts are the salts of the polycarboxylic acids such as citric acid, adipic acid, succinic acid, glutaric acid, tartaric acid, sugar acids, and mixtures thereof. The acids per se may also be used. In addition to their builder effect, the acids typically also possess the property of an acidifying component and thus also serve, as for example in the granules of the invention, to establish a lower and milder pH of laundry detergents and cleaning products. In this context, mention may be made in particular, of citric acid, succinic acid, glutaric acid, adipic acid, gluconic acid, and any desired mixtures thereof.

Also suitable as organic builders are polymeric poly-carboxylates; these are, for example, the alkali metal salts of polyacrylic acid or of polymethacrylic acid, examples being those having a relative molecular mass of from 5.00 to 70,000 g/mol. The molar masses reported for polymeric polycarboxylates, for the purposes of this document, are weight-average molecular masses, $M_w$, of the respective acid form, determined basically by means of gel permeation chromatography (GPC) using a UV detector. The measurement was made against an external polyacrylic acid standard, which owing to its structural similarity to the polymers under investigation provides realistic molar weight values. These figures differ markedly from the molar weight values obtained using polystyrenesulfonic acids as the standard. The molar masses measured against polystyrenesulfonic acids are generally much higher than the molar masses reported in this document.

The inventive compositions and especially support materials may also comprise polymers. Suitable polymers, which can also be used as support materials in conjunction with fragrances, comprise, in particular, polyacrylates, which preferably have a molecular mass of from 2,000 to 20,000 g/mol. Owing to their superior solubility, preference in this group may be given in turn to the short-chain polyacrylates, which have molar masses of from 2,000 to 10,000 g/mol, and with particular preference from 3,000 to 5,000 g/mol.

Also suitable are copolymeric polycarboxylates, especially those of acrylic acid with methacrylic acid and of acrylic acid or methacrylic acid with maleic acid. Copolymers which have been found particularly suitable are those of acrylic acid with maleic acid which contain from 50 to 90% by weight acrylic acid and from 50 to 10% by weight maleic acid. Their relative molecular mass, based on free acids, is generally from 2,000 to 70,000 g/mol, preferably from 20,000 to 50,000 g/mol, and in particular, from 30,000 to 40,000 g/mol.

The amount of organic builder substances in the compositions may vary within a broad spectrum. Preference is given to amounts of from 2 to 20% by weight; in particular, amounts of not more than 10% by weight are particularly well received.

The compositions of the invention may possess components from the classes of the graying inhibitors (soil carriers), the neutral salts, and/or the textile softener auxiliaries (e.g., cationic surfactants), and preferably do so.

The function of graying inhibitors is to keep the soil detached from the fiber in suspension in the liquor and so to prevent redeposition of the soil. Suitability for this purpose is possessed by water-soluble colloids, usually organic in nature, examples being the water-soluble salts of polymeric carboxylic acids, size, gelatin, salts of ethercarboxylic acids or ethersulfonic acids of starch or of cellulose, or salts of acidic sulfuric esters of cellulose or of starch. Water-soluble polyamides containing acidic groups are also suitable for this purpose. Additionally it is possible to use soluble starch preparations and starch products other than those mentioned above, e.g., degraded starch, aldehyde starches, and so on. Polyvinylpyrrolidone as well can be used. Preference, however, is given to employing cellulose ethers, such as carboxymethylcellulose (Na salt), methylcellulose, hydroxyalkylcellulose, and mixed ethers, such as methylhydroxyethylcellulose, methylhydroxypropylcellulose, methylcarboxymethylcellulose, and mixtures thereof, and also polyvinylpyrrolidone, in amounts, for example, of from 0.1 to 5% by weight, based on the compositions.

A typical example of a suitable representative of the neutral salts is the compound sodium sulfate. It can be used in amounts of, for example, 0 to 60%, preferably from 2 to 45% by weight.

Examples of suitable softeners, described in more detail later on below, are, for example, swellable phyllosilicates of the type of corresponding montmorillonites, bentonite for example, and cationic surfactants.

The amount of water in the composition depends on factors including that of whether the composition is in liquid or solid form, and is therefore preferably 0 to less than 100% by weight and in particular, 0.5% to 95% by weight, particular preference being given to values of not more than 5% by weight particularly in the case of solid or nonaqueous liquid compositions. In the case of solid compositions, these figures do not include the water adhering to any aluminosilicates present, such as zeolite.

In the case of liquid compositions, the composition of the invention contains water, according to one preferred embodiment, in an amount of more than 20%, advantageously more than 30%, more advantageously more than 40%, more advantageously still more than 50%, in particular, 60% to 95%, with particular preference 70% to 93%, and most preferably 80% to 90% by weight.

Where it is a solid, the composition of the invention may have an outstanding free-flow behavior.

Where the composition is in particulate form, the particles can be after-treated, by for example rounding the particles in the composition. Rounding may take place in a typical spheronizer. The rounding time is preferably not longer than 4 minutes, in particular, not longer than 3.5 minutes. Rounding times of not more than 1.5 minutes or below are particularly preferred. Rounding achieves a further increase in the uniformity of the grain spectrum, since any agglomerates formed are comminuted.

A composition of the invention in particle form can be after-treated in particular, with nonionic surfactants, perfume and/or foam inhibitors, or preparation forms comprising these ingredients, preferably with amounts up to 20% by weight of active substance, in particular, with amounts of 2% to 18% by weight of active substance, based in each case on the after-treated product, in a way which is typical per se, preferably in a mixer or, where appropriate, in a fluidized bed.

In particular, it is possible for a composition of the invention likewise to be powdered or after-treated with solids, preferably in amounts up to 15% by weight, in particular, in amounts from 2% to 15% by weight, based in each case on the total weight of the after-treated composition.

Solids which can be used for the after-treatment include, preferably, bicarbonate, carbonate, zeolite, silica, citrate, urea or mixtures of these, especially in amounts from 2% to 15% by weight, based on the total weight of the after-treated product. The after-treatment can be carried out advantageously in a mixer and/or using a spheronizer.

In one preferred embodiment of the invention a composition of the invention, after-treated with nonionic surfactants, which may for example also include optical brighteners and/or hydrotropes, perfume, preferably comprising the fragrance preparation of the invention, and/or a solution of optical brightener and/or foam inhibitors or preparation forms which may include these ingredients. These ingredients, or preparation forms including these ingredients, are preferably applied in liquid, melted or pasty form to the particulate composition that is to be after-treated.

It is preferred in this context to carry out the after treatment with the stated substances in a typical mixer, merely by way of example in a twin-screw mixer, over the course of a maximum of 1 minute, preferably over the course of 30 seconds, and, for example, over the course of 20 seconds, the time indications standing at the same time for addition time and mixing time.

In the text below, the nonionic surfactants are described in more detail. These nonionic surfactants can be applied to the particulate compositions in an after-treatment step. Of course, however, it is possible with advantage for all of the nonionic surfactants to be included directly in the composition of the invention, which can be liquid or solid or in the form of a foam or gel.

Nonionic surfactants used are preferably alkoxylated, advantageously ethoxylated, especially primary, alcohols having preferably 8 to 18 carbon atoms and on average from 1 to 12 mol of ethylene oxide (EO) per mole of alcohol, in which the alcohol radical may be linear or, preferably, methyl-branched in position 2 and/or may comprise linear and methyl-branched radicals in a mixture, as are commonly present in oxo alcohol radicals. In particular, however, preference is given to alcohol ethoxylates containing linear radicals from alcohols of natural origin having 12 to 18 carbon atoms, e.g., from coconut, palm, palm kernel, tallow fatty or oleyl alcohol, and on average from 2 to 8 EO per mole of alcohol. Preferred ethoxylated alcohols include, for example, $C_{12}$-$C_{14}$ alcohols containing 3 EO or 4 EO, $C_9$-$C_{11}$ alcohols containing 7 EO, $C_{13}$-$C_{15}$ alcohols containing 3 EO, 5 EO, 7 EO or 8 EO, $C_{12}$-$C_{18}$ alcohols containing 3 EO, 5 EO or 7 EO, and mixtures thereof, such as mixtures of $C_{12}$-$C_{14}$ alcohol containing 3 EO and $C_{12}$-$C_{18}$ alcohol containing 7 EO. The stated degrees of ethoxylation represent statistical mean values, which for a specific product may be an integer or a fraction.

Preferred alcohol ethoxylates have a narrowed homolog distribution (narrow range ethoxylates, NREs). In addition to these nonionic surfactants it is also possible to use fatty alcohols containing more than 12 EO. Examples thereof are (tallow) fatty alcohols containing 14 EO, 16 EO, 20 EO, 25 EO, 30 EO or 40 EO.

Preferred nonionic surfactants are one or more unbranched or branched, saturated or unsaturated $C_{10-22}$ alcohols which are alkoxylated with ethylene oxide (EO) and/or propylene oxide (PO) and have a degree of alkoxylation of up to 30, preferably ethoxylated $C_{10-18}$ fatty alcohols having a degree of ethoxylation of less than 30, preferably 1 to 20, in particular, 1 to 12, more preferably 1 to 8, very preferably 2 to 5, examples being $C_{12-14}$ fatty alcohol ethoxylates with 2, 3 or 4 EO or a mixture of the $C_{12-14}$ fatty alcohol ethoxylates with 3 and 4 EO in a weight ratio of 1:1, or isotridecyl alcohol ethoxylate with 5, 8 or 12 EO as described, for example, in DE 40 14 055 C2 (Grillo-Werke), to which reference is made in this respect and the content of which is hereby incorporated into this application.

As further nonionic surfactants, furthermore, use may also be made of alkyl glycosides of the general formula $RO(G)_x$, where R is a primary straight-chain or methyl-branched aliphatic radical, especially an aliphatic radical methyl-branched in position 2, having 8 to 22, preferably 12 to 18, carbon atoms, and G is the symbol representing a glycose unit having 5 or 6 carbon atoms, preferably glucose. The degree of oligomerization, x, which indicates the distribution of monoglycosides and oligoglycosides, is any desired number between 1 and 10; preferably, x is from 1.1 to 1.4.

A further class of nonionic surfactants used with preference, which are used either as sole nonionic surfactant or in combination with other nonionic surfactants, in particular, together with alkoxylated fatty alcohols and/or alkylglycosides, are alkoxylated, preferably ethoxylated, or ethoxylated and propoxylated, fatty acid alkyl esters, preferably having 1 to 4 carbon atoms in the alkyl chain, especially fatty acid methyl esters, as described, for example, in Japanese Patent Application No. JP 58/217598 or which are preferably prepared in accordance with the method described in International Patent Application No. WO-A-90/13533. Particular preference is given to $C_{12}$-$C_{18}$ fatty acid methyl esters containing on average from 3 to 15 EO, in particular, containing on average from 5 to 12 EO.

Nonionic surfactants of the amine oxide type, examples being N-cocoalkyl-N,N-dimethylamine oxide and N-tallowalkyl-N,N-dihydroxyethylamine oxide, and of the fatty acid alkanolamide type, may also be suitable. The amount of these nonionic surfactants is preferably not more than that of the ethoxylated fatty alcohols, in particular, not more than half thereof.

Also suitable are alkoxylated amines, advantageously ethoxylated and/or propoxylated, especially primary and secondary, amines having preferably 1 to 18 carbon atoms per alkyl chain and on average 1 to 12 mol of ethylene oxide (EO) and/or 1 to 10 mol of propylene oxide (PO) per mole of amine.

In the case of compositions of the invention that are suitable in particular, for machine dishwashing, particularly dishwash detergents in the form of shaped tablet bodies, such as tabs, suitable surfactants include in principle all surfactants. Preference for this end use, however, is given to the nonionic surfactants described above, and, of those, in particular, to the low-foaming nonionic surfactants. The alkoxylated alcohols are particularly preferred, especially the ethoxylated and/or propoxylated alcohols. By alkoxylated alcohols the skilled worker understands, in general, the reaction products of alkylene oxide, preferably ethylene oxide, with alcohols, preferably, for the purposes of the present invention, the relatively long-chain alcohols ($C_{10}$ to $C_{18}$, preferably between $C_{12}$ and $C_{16}$, such as $C_{11}$, $C_{12}$, $C_{13}$, $C_{14}$, $C_{15}$, $C_{16}$, $C_{17}$, and $C_{18}$ alcohols, for example). Generally speaking, n moles of ethylene oxide and one mole of alcohol produce, depending on the reaction conditions, a complex mixture of addition products differing in degree of ethoxylation. A further embodiment consists in the use of mixtures of the alkylene oxides, preferably of the mixture of ethylene oxide and propylene oxide. A further possibility if desired is to obtain, by a final etherification with short-chain alkyl groups, such as preferably the butyl group, the class of substance of the "capped" alcohol ethoxylates, which can likewise be used for the purposes of the invention. Very particular preference is given in this context, for the purposes of the present invention, to highly ethoxylated fatty alcohols or mixtures thereof with endgroup-capped fatty alcohol ethoxylates.

The compositions of the invention may advantageously further comprise foam inhibitors, such as, for example, foam-inhibiting paraffin oil or foam-inhibiting silicone oil, dimethylpolysiloxane for example. Also possible is the use of mixtures of these active substances. Suitable additives which are solid at room temperature, particularly in the case of the stated foam-inhibiting active substances, include paraffin waxes, silicas, which may also be conventionally hydrophobicized, and bisamides derived from $C_{2-7}$ diamines and $C_{12-22}$ carboxylic acids.

Foam-inhibiting paraffin oils suitable for use, which may be present as a blend with paraffin waxes, are generally complex mixtures of substances without a defined melting point. For their characterization, the melting range is usually determined by means of differential thermoanalysis (DTA), as described in "The Analyst" 87 (1962), 420, and/or the solidification point. By this is meant the temperature at which the paraffin undergoes the transition from the liquid state to the solid state by slow cooling. Paraffins having less than 17 carbon atoms cannot be used in accordance with the invention, and their fraction in the paraffin oil mixture ought therefore to be as low as possible, and is preferably below the limit which can be measured significantly by customary analytic methods, gas chromatography for example. It is preferred to use paraffins which solidify in the range from 20° C. to 70° C. It should be borne in mind here that even paraffin wax mixtures which appear solid at room temperature may contain different fractions of liquid paraffin oils. In the case of the paraffin waxes which can be used in accordance with the invention the liquid fraction at 40° C. is as high as possible, without already amounting to 100% at this temperature. Preferred paraffin wax mixtures have at 40° C. a liquid fraction of at least 50% by weight, in particular, from 55% by weight to 80% by weight, and at 60° C. have a liquid fraction of at least 90% by weight. As a result of this the paraffins are fluid and pumpable at temperatures down to at least 70° C., preferably down to at least 60° C. It should further be ensured that the paraffins as far as possible contain no volatile fractions. Preferred paraffin waxes contain less than 1% by weight, in particular, less than 0.5% by weight, of fractions which can be evaporated at 110° C. under atmospheric pressure. Paraffins which can be used in accordance with the invention can be acquired, for example, under the commercial designations Lunaflex® from Fuller and Deawax® from DEA Mineralöl AG.

The paraffin oils may comprise bisamides which are solid at room temperature and derive from saturated fatty acids having 12 to 22, preferably 14 to 18, carbon atoms and also from alkylene diamines having 2 to 7 carbon atoms. Suitable fatty acids are lauric, myristic, stearic, arachidic, and behenic acid, and also mixtures thereof, such as are obtainable from natural fats or hydrogenated oils, such as tallow or hydrogenated palm oil. Examples of suitable diamines include ethylenediamine 1,3-propylenediamine, tetramethylenediamine, pentamethylenediamine, hexamethylenediamine, p-phenylenediamine, and tolylenediamine. Preferred diamines are ethylenediamine and hexamethylenediamine. Particularly preferred bisamides are bismyristoylethylenediamine, bispalmitoylethylenediamine, bisstearoylethylenediamine, and mixtures thereof, and also the corresponding derivatives of hexamethylenediamine.

The composition and/or the after-treated compositions described above can preferably be mixed with further constituents, particularly those of detergents and/or care products. From the broad state of the art it is common knowledge as to which ingredients of detergents and which raw materials can typically be further admixed. Examples of those in question include substances such as bleaches, bleach activators and/or bleaching catalysts, enzymes, temperature-sensitive dyes, and so on, which of course may also be present directly in the composition.

With preference it is possible for the composition to include UV absorbers, which advantageously attach to the treated textiles and improve the light stability of the fibers and/or the light stability of other formulation constituents. By UV absorbers are meant organic substances (light protection filters) which are able to absorb ultraviolet radiation and to emit the absorbed energy again in the form of radiation of longer wavelength, e.g., heat. Compounds which possess these desired properties are, for example, the compounds of benzophenone, which are active by radiationless deactivation and derivatives of benzophenone having substituents in position 2 and/or 4. Also suitable, furthermore, are substituted benzotriazoles, acrylates phenyl-substituted in position 3 (cinnamic acid derivatives), with or without cyano groups in position 2, salicylates, organic Ni complexes, and natural substances such as umbelliferone and the endogenous urocanic acid. Particular importance is possessed by biphenyl derivatives and, in particular, stilbene derivatives as described, for example, in EP 0728749 A and are available commercially as Tinosorb® FD or Tinosorb® FR from Ciba. As UV-B absorbers mention may be made of 3-benzylidenecamphor or 3-benzylidenenorcamphor and its derivatives, e.g., 3-(4-methylbenzylidene)camphor as described in European Patent No. EP 0693471 B1; 4-aminobenzoic acid derivatives, preferably 2-ethylhexyl 4-(dimethylamino)benzoate, 2-octyl 4-(dimethylamino)benzoate, and amyl 4-(dimethylamino)benzoate; esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylenes); esters of salicylic acid, preferably 2-ethylhexyl salicylate, 4-isopropylbenzyl salicylate, homomethyl salicylate; derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzalmalonic acid, preferably di-2-ethylhexyl 4-methoxybenzmalonate; triazine derivatives, such as, for example 2,4,6-trianilino(p-carbo-2'-ethyl-1'-hexyloxy)-1,3,5-triazine and Octyl Triazone as described in EP 0818450 A1, or Dioctyl Butamido Triazone (Uvasorb® HEB); propane-1,3-diones, such as 1-(4-tert-butylphenyl)-3-(4'-methoxyphenyl)propane-1,3-dione, for example; ketotricyclo[5.2.1.0]decane derivatives as described in EP 0694521 B1. Of further suitability are 2-phenylbenzimidazole-5-sulfonic acid and the alkali metal, alkaline earth metal, ammonium, alkylammonium, alkanolammonium, and glucammonium salts thereof; sulfonic acid derivatives of benzophenones, preferably 2-hydroxy-4-methoxybenzophenone-5-sulfonic acid and its salts; sulfonic acid derivatives of 3-benzylidenecamphor, such as 4-(2-oxo-3-bornylidenemethyl)benzenesulfonic acid and 2-methyl-5-(2-oxo-3-bornylidene)sulfonic acid, for example, and salts thereof.

As typical UV-A filters, suitability is possessed in particular, by derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol 1789), 1-phenyl-3-(4'-isopropylphenyl)propane-1,3-dione, and enamine compounds, as described in German Patent No. DE 19712033 A1 (BASF). The UV-A and UV-B filters can of course also be used in mixtures. Besides the stated soluble substances, insoluble light protection pigments as well are suitable for this purpose, namely finely disperse, preferably nanoized, metal oxides and/or salts. Examples of suitable metal oxides are, in particular, zinc oxide and titanium dioxide and, in addition, oxides of iron, of zirconium, of silicon, of manganese, of aluminum, and of cerium, and also mixtures thereof. Salts which can be used include silicates (talc), barium sulfate or zinc stearate. The oxides and salts are already used, in the form of a pigment, for skincare emulsions, skin protection emulsions, and decorative cosmetics. The particles ought to have an average diameter of less than 100 nm, preferably between 5 and 50 nm, and in particular, between 15 and 30 nm. They may have a spherical form, although it is also possible to employ particles which possess a form which is ellipsoidal or which otherwise deviates from the spherical. The pigments may also be in surface-treated form, i.e., hydrophilicized or hydrophobicized. Typical examples are coated titanium dioxides, such as titanium dioxide T 805 (Degussa) or Eusolex® T2000 (Merck), for example. Suitable hydrophobic coating agents in this case include, in particular, silicones, and especially trialkoxyoctylsilanes or simethicones. It is preferred to use micronized zinc oxide. Further suitable UV light protection filters can be found in the review by P. Finkel in SÖFW-Journal 122, 543 (1996).

The UV absorbers are advantageously present in the composition in amounts of from 0.01% by weight to 5% by weight, preferably from 0.03% by weight to 1% by weight. They may also be admixed to the composition subsequently, together for example with other substances.

The compositions of the invention may with preference, where they are solid, take the form of tablets. Tablets for the purposes of the present specification, irrespective of the nature of their production, are dimensionally stable, solid bodies. Bodies of this kind can be produced, for example, by crystallization, casting, injection molding, reactive or thermal sintering, (co)extrusion, prilling, pelletizing, or compacting methods such as calendering or tableting. The production of the tablets by tableting is particularly preferred in the context of the present specification. The tablet is therefore composed preferably of compressed particulate material.

Inventive compositions in solid form, preferably in the form of tablets, may preferably include disintegration assistants. Examples of suitable swellable disintegration assistants include bentonites or other swellable silicates. Synthetic polymers can be used as well, especially the crosslinked polyvinylpyrrolidone or the superabsorbents that are used in the hygiene sector.

Swellable disintegration assistants used with particular advantage are polymers based on starch and/or cellulose. These base substances may be processed, alone or in a mixture with further natural and/or synthetic polymers, to provide swellable disintegrants. In the simplest case, a cellulosic material or pure cellulose can be converted by granulation, compacting or other application of pressure into secondary particles, which on contact with water swell and so act as disintegrants. Suitable cellulosic material found has been wood pulp, which is obtainable by thermal or chemothermal methods from wood or woodchips (sawn chips, sawhouse wastes). This cellulose material from the TMP process (thermomechanical pulp) or from the CTMP process (chemothermomechanical pulp) can then be compacted by application of pressure, preferably roll-compacted, and converted into particle form. In exactly the same way it is of course also possible to use pure cellulose, although this is more expensive owing to its raw material basis. In that case it is possible to use not only microcrystalline cellulose but also amorphous, finely divided cellulose and mixtures thereof.

Another way is to granulate the cellulosic material with addition of granulating assistants. Examples of granulating assistants that have been found suitable include solutions of synthetic polymers, or nonionic surfactants. In order to avoid residues on textiles washed with the compositions of the invention, the primary fiber length of the cellulose used or of the cellulose in the cellulosic material would be below 200 μm, preference being given to primary fiber lengths below 100 μm and in particular, below 50 μm.

The secondary particles ideally possess a particle size distribution in which preferably more than 90% by weight of the particles have sizes above 200 μm. A certain dust fraction can contribute to improved stability of the thus-produced tablets on storage. Amounts of a fine dust fraction of less than 0.1 mm of up to 10% by weight, preferably up to 8% by weight, may be present in the inventively employed compositions containing disintegrant granules.

In addition it is possible for the compositions of the invention to be present in the form of a conditioning composition and/or conditioning substrate and to include corresponding components, as described in particular, in Published International Application No. WO 03/038022 A1, to which reference is made in its entirety herein. Conditioning for the purposes of this invention refers preferably to the finish-imparting treatment of textiles, materials and fabrics. The conditioning gives the textiles positive properties, such as an improved soft hand, increased gloss and color brightness, an improved fragrance sensation, a reduction in felting, greater ease of ironing through a reduction in slip properties, a reduction in creasing and in static charging, and also inhibition of color transfer in the case of dyed textiles.

Compositions of the invention, especially conditioning compositions, may for example comprise polymerizable betaine esters of the general formula (I):

$$[R^a—X—(CH_2)_k—NR^bR^c—(CR^dR^e)_l—(C{=}O)—O—(R^f—O)_m—R^g]^{(+)}A^{(-)} \quad (I)$$

in which $R^a$ is an ethylenically unsaturated radical containing at least one carbonyl function, such as acryloyl, methacryloyl, maleoyl or itaconoyl, for example;

X is an oxygen atom, —N($CH_3$)— or —NH—;

$R^b$, $R^c$ independently of one another are unbranched or branched alkyl radicals having 1 to 4 carbon atoms, and may contain heteroatom substituents, especially O, S, N, P;

the radicals $R^d$, $R^e$ are selected independently of one another from hydrogen (H), unbranched or branched alkyl radicals having 1 to 4 carbon atoms, unsubstituted or substituted aryl or benzyl radicals, and —$CH_2COOH$, —$CH_2COOR$, —$CH_2CH_2COOH$, —$CH_2CH_2COOR$; R denotes linear or branched and/or cyclic and/or substituted hydrocarbon radicals which may contain multiple bonds, which may contain halogen atoms and/or heteroatoms and/or carbonyl groups, and which have 1 to 18 carbon atoms, or else R is a polyether composed exclusively of ethylene oxide or propylene oxide or butylene oxide or styrene oxide;

$R^f$ is a branched and/or substituted and/or cyclic hydrocarbon radical which may contain multiple bonds and has 1 to 10, preferably 2 or 3, carbon atoms, or is a styrene radical, or is composed exclusively of ethylene or propylene or butylene or styrene radicals, or is a block copolymer or random copolymer containing the aforementioned radicals;

$R^g$ is an unbranched or branched, optionally cyclic hydrocarbon radical which may contain double bonds and has 1 to 22 carbon atoms, $R^g$ being an unbranched or branched hydrocarbon radical that may contain double bonds when m is=0, and it being possible for $R^g$ to be H when m is >0;

k, l independently of one another are 1 to 4, k being preferably 2 or 3 and l being preferably 1; and m has a value between 0 to 100, preferably 0 to 40;

$A^{(-)}$ is an anion; and/or homopolymers prepared from polymerizable betaine esters of the general formula (I), and copolymers prepared from polymerizable betaine esters of the general formula (I) and suitable comonomers of the general formula (II).

$$R^wR^zC{=}CR^xR^y \quad (II)$$

in which $R^x$ and $R^y$ are H, $R^w$ is H or $CH_3$, and $R^z$ is a radical containing at least one carbonyl group, such as —C(O)OR, —C(O)NR'R", for example, where R, R' and R" are H or linear or branched and/or cyclic and/or substituted hydrocarbon radicals which may contain multiple bonds, may contain halogen atoms and/or heteroatoms and/or carbonyl groups, and have 1 to 18 carbon atoms; or in which $R^w$ and $R^x$ are H, $R^y$ and $R^z$ are radicals containing a carbonyl group, such as —C(O)OR, —C(O)NR'R", for example, where R, R' and R" are H or linear or branched and/or cyclic, aliphatic or aromatic and/or substituted hydrocarbon radicals which may contain multiple bonds, may contain halogen atoms and/or heteroatoms, and have 1 to 18 carbon atoms;

or in which $R^w$, $R^x$ and $R^y$ are H and $R^z$ is an aromatic or heteroaromatic which optionally is halogen atom-substituted and/or heteroatom-substituted and contains linear and/or branched alkyl substituents;

or in which $R^w$, $R^x$ and $R^y$ are H and $R^z$ is $-(CH_2)_a-OR^{III}$, where $R^{III}$ is H or an alkyl radical optionally containing carbonyl groups and having 1 to 22 carbon atoms, or a polyether composed exclusively of ethylene oxide or propylene oxide or butylene oxide or styrene oxide and represents a block or random copolymer that contains the stated radicals, and a is 0 or 1.

The aforementioned polymerizable betaine esters of the formula (I) and/or the polymeric betaine esters, which in the case of the homopolymers are prepared from the monomeric polymerizable betaine esters of the general formula (I) and/or in the case of the copolymers are prepared from polymerizable betaine esters of the general formula (I) and suitable comonomers of the general formula (II), may in accordance with the invention be used preferably in conditioning compositions. Particularly stable, and therefore likewise preferable for use as conditioning compositions, are the polymerizable betaine esters of the general formula (I) and/or the polymeric betaine esters, which in the case of the homopolymers are prepared from the monomeric polymerizable betaine esters of the general formula (I) and/or in the case of the copolymers are prepared from polymerizable betaine esters of the general formula (I) and suitable comonomers of the general formula (II), for which X is $-N(CH_3)-$ or —NH—.

With preference it is possible for the compositions of the invention, especially conditioning compositions, to include oligomers and polymers prepared by copolymerizing 0.5 to 100 mol % of a polymerizable betaine ester of the general formula (I) (at 100 mol % the compounds in question are homopolymers) and 0 to 99.5 mol % of an ethylenically unsaturated comonomer of the general formula (II), preferably prepared by copolymerizing 20 to 70 mol % of a polymerizable betaine ester of the general formula (I) and 30 to 80 mol % of an unsaturated comonomer of the general formula (II), more preferably prepared by copolymerizing 40 to 60 mol % of a polymerizable betaine ester of the general formula (I) and 60 to 40 mol % of an ethylenically unsaturated comonomer of the general formula (II). Uttermost preference is given to homopolymers prepared from polymerizable betaine esters of the formula (I) for use in the compositions of the invention. The homopolymers offer the advantage that they carry a higher content of esterified active alcohols and, moreover, exhibit improved attachment behavior and hence improved textile-conditioning properties, such as soft fabric hand, for instance. Where X is=$-N(CH_3)-$ or —NH—, moreover, the polymers exhibit particularly good stability to hydrolysis, leading to a desired slow—i.e., retarded—release of the esterified fragrances. Homopolymers in which k is=3 are particularly advantageous. Polymerizable betaine esters of the formula (I) and polymeric betaine esters preparable from them that have been found particularly suitable are those in which m is=0 and $R^g$ is a fragrance alcohol.

Compositions of the invention, especially conditioning compositions, may comprise polymerizable betaine esters of the formula (I) and/or polymeric betaine esters, which in the case of the homopolymers are prepared from the monomeric polymerizable betaine esters of the general formula (I) and/or in the case of the copolymers are prepared from polymerizable betaine esters of the general formula (I) and suitable comonomers of the general formula (II), in which $R^g$ is an aromatic fragrance alcohol. Alcohols considered to be particularly preferred fragrance alcohols are therefore phenylethanol, phenoxyethanol, 2-phenylpropanol, 3-phenylpropanol, α-methylbenzyl alcohol, amyl salicylate, benzyl alcohol, benzyl salicylate, butyl salicylate, cyclohexyl salicylate, dimethylbenzylcarbinol, ethyl salicylate, ethylvanillin, eugenol, hexyl salicylate, isoeugenol, phenol, phenyl salicylate, thymol, vanillin, cinnamyl alcohol, and 3-methyl-5-phenyl-1-pentanol.

The aforementioned selection does not, however, represent any restriction with regard to the aromatic fragrance alcohols that are suitable.

Inventive compositions, especially conditioning compositions, may advantageously have a pH of less than or equal to 8, preferably less than 7, more preferably between 1 and 6, and in particular, between 2 and 5.

The conditioning compositions of the invention may in one preferred embodiment further comprise surfactants. The further use of surfactants has the effect of reinforcing the conditioning properties and, moreover, contributes to improved storage stability and dispersibility or emulsifiability of the individual components of the conditioning composition.

For the purpose of improving the soft hand and the finishing properties, the compositions of the invention may comprise softener components. Examples of such compounds are quaternary ammonium compounds, cationic polymers and emulsifiers, as are used in haircare compositions and also in compositions for textile finishing. These softening compounds, which are also described in greater detail below, can be present in all compositions of the invention, but particularly in the conditioning compositions and in compositions aiming to achieve a softening effect.

Suitable examples are quaternary ammonium compounds of the formulas (III) and (IV)

(III)

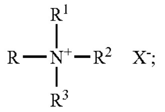

(IV)

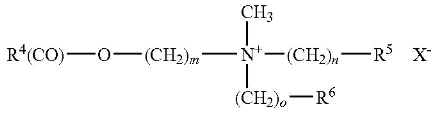

where, in (III), R and $R^1$ are an acyclic alkyl radical having 12 to 24 carbon atoms, $R^2$ is a saturated $C_1$-$C_4$-alkyl or hydroxyalkyl radical, $R^3$ is either R, $R^1$ or $R^2$ or is an aromatic radical, $X^-$ is either a halide, methosulfate, methophosphate or phosphate ion and mixtures thereof. Examples of cationic compounds of the formula (III) are didecyldimethylammonium chloride, ditallow-dimethylammonium chloride or dihexadecylammonium chloride.

Compounds of the formula (IV) are so-called ester quats. Ester quats are characterized by excellent biodegradability. Here, $R^4$ is an aliphatic alkyl radical having 12 to 22 carbon atoms with 0, 1, 2 or 3 double bonds; $R^5$ is H, OH or O(CO) $R^7$, $R^6$ is, independently of $R^5$, H, OH or O(CO)$R^3$, where $R^7$ and $R^8$, independently of one another, are each an aliphatic alkenyl radical having 12 to 22 carbon atoms with 0, 1, 2 or 3 double bonds. m, n and p can each, independently of one another, have the value 1, 2 or 3. $X^-$ can either be a halide, methosulfate, methophosphate or phosphate ion or mixtures thereof. Preference is given to compounds which contain the group O(CO)$R^7$ for $R^5$, and alkyl radicals having 16 to 18 carbon atoms for $R^4$ and $R^7$. Particular preference is given to compounds in which $R^6$ is also OH. Examples of compounds of the formula (IV) are methyl-N-(2-hydroxyethyl)-N,N-di (tallow-acyloxy-ethyl)ammonium methosulfate, bis(palmitoyl)ethylhydroxyethylmethylammonium methosulfate or methyl-N,N-bis(acyloxyethyl)-N-(2-hydroxyethyl)ammonium methosulfate. If quaternized compounds of the formula (IV) which have unsaturated alkyl chains are used, preference is given to the acyl groups whose corresponding fatty acids have an iodine number between 5 and 80, preferably between 10 and 60 and in particular, between 15 and 45 and which have a cis/trans isomer ratio (in % by weight) greater than 30:70, preferably greater than 50:50 and in particular, greater than 70:30. Standard commercial examples are the methylhydroxyalkyldialkoyloxyalkylammonium methosulfates sold by Stepan under the trade name Stepantex®, or the products from Cognis known under Dehyquart® or the products from Goldschmidt-Witco known under Rewoquat®. Further preferred compounds are the diester quats of the formula (V), which are available under the name Rewoquat® W 222 LM or CR 3099 and, as well as softening, also ensure stability and color protection.

(V)

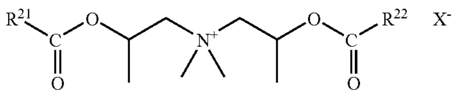

$R^{21}$ and $R^{22}$ are, independently of one another, each an aliphatic radical having 12 to 22 carbon atoms with 0, 1, 2 or 3 double bonds.

As well as the above-described quaternary compounds, other known compounds can also be used, such as, for example, quaternary imidazolinium compounds of the formula (VI), (VI)

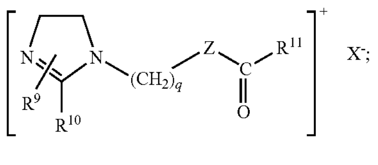

where $R^9$ is H or a saturated alkyl radical having 1 to 4 carbon atoms, $R^{10}$ and $R^{11}$, independently of one another, are each an aliphatic, saturated or unsaturated alkyl radical having 12 to 18 carbon atoms, $R^{10}$ may alternatively also be O(CO)$R^{20}$, where $R^{20}$ is an aliphatic, saturated or unsaturated alkyl radical having 12 to 18 carbon atoms, and Z is an NH group or oxygen and $X^-$ is an anion. q can assume integral values between 1 and 4.

Further suitable quaternary compounds are described by formula (VII), (VII)

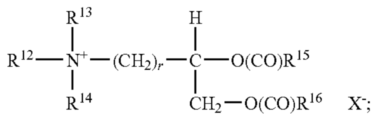

where $R^{12}$, $R^{13}$ and $R^{14}$, independently of one another, are a $C_{1-4}$-alkyl, alkenyl or hydroxyalkyl group, $R^{15}$ and $R^{16}$ are each, chosen independently, a $C_{8-28}$-alkyl group and r is a number between 0 and 5.

As well as the compounds of the formulas (III) and (IV), short-chain, water-soluble, quaternary ammonium compounds can also be used, such as trihydroxyethylmethylammonium methosulfate or the alkyltrimethylammonium chlorides, dialkyldimethylammonium chlorides and trialkylmethylammonium chlorides, e.g., cetyltrimethylammonium chloride, stearyltrimethylammonium chloride, distearyldimethylammonium chloride, lauryldimethylammonium chloride, lauryldimethylbenzylammonium chloride and tricetylmethylammonium chloride.

Protonated alkylamine compounds which have a softening action, and the nonquaternized, protonated precursors of the cationic emulsifiers, are also suitable.

Further cationic compounds which can be used according to the invention represent the quaternized protein hydrolyzates.

Suitable cationic polymers include the polyquaternium polymers, as specified in the CTFA Cosmetic Ingredient Dictionary (The Cosmetic, Toiletry and Fragrance, Inc., 1997), in particular, the polyquaternium-6, polyquaternium-7, and polyquaternium-10 polymers (Ucare Polymer IR 400; Amerchol), also referred to as merquats, polyquaternium-4 copolymers, such as graft copolymers with a cellulose backbone and quaternary ammonium groups which are bonded via allyldimethylammonium chloride, cationic cellulose derivatives, such as cationic guar, such as guar hydroxypropyltriammonium chloride, and similar quaternized guar derivatives (e.g., Cosmedia Guar, manufacturer: Cognis GmbH), cationic quaternary sugar derivatives (cationic alkyl polyglucosides), e.g., the commercial product Glucquat® 100, according to CTFA nomenclature a "Lauryl Methyl Gluceth-10 Hydroxypropyl Dimonium Chloride," copolymers of PVP and dimethylaminomethacrylate, copolymers of vinylimidazole and vinylpyrrolidone, aminosilicone polymers and copolymers.

It is likewise possible to use polyquaternized polymers (e.g., Luviquat Care from BASF) and also cationic biopolymers based on chitin, and derivatives thereof, for example the polymer obtainable under the trade name Chitosan® (manufacturer: Cognis).

Likewise useful according to the invention are cationic silicone oils, such as, for example, the commercially available products Q2-7224 (manufacturer: Dow Corning; a stabilized trimethylsilylamodimethicone), Dow Corning 929 emulsion (comprising a hydroxylamino-modified silicone, which is also referred to as amodimethicone), SM-2059 (manufacturer: General Electric), SLM-55067 (manufacturer: Wacker) Abil®-Quat 3270 and 3272 (manufacturer: Goldschmidt-Rewo; diquaternary polydimethylsiloxanes, quaternium-80) and Siliconquat Rewoquat® SQ 1 (Tegopren® 6922, manufacturer: Goldschmidt-Rewo).

It is likewise possible to use compounds of the formula (VIII)

(VIII)

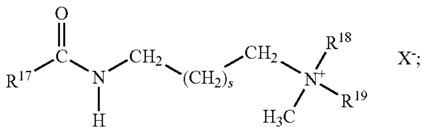

which may be alkylamidoamines in their nonquaternized or, as shown, their quaternized form. $R^{17}$ may be an aliphatic alkenyl radical having 12 to 22 carbon atoms with 0, 1, 2 or 3 double bonds. s can assume values between 0 and 5. $R^{18}$ and $R^{19}$ are, independently of one another, each H, $C_{1-4}$-alkyl or hydroxyalkyl. Preferred compounds are fatty acid amidoamines, such as the stearylamidopropyldimethylamine obtainable under the name Tego Amid® S 18, or the 3-tallowamidopropyltrimethylammonium methosulfate obtainable under the name Stepantex® X 9124, which are characterized not only by a good conditioning effect but also by color-transfer-inhibiting effect and in particular, by their good biodegradability.

Particular preference is given to alkylated quaternary ammonium compounds in which at least one alkyl chain is interrupted by an ester group and/or amido group, in particular, N-methyl-N-(2-hydroxyethyl)-N,N-(ditallow-acyl-oxyethyl)ammonium methosulfate.

Suitable nonionic softeners are primarily polyoxyalkylene glycerol alkanoates, as are described in British Patent specification GB 2,202,244, polybutylenes, as are described in British Patent specification GB 2,199,855, long-chain fatty acids, as are described in European Patent No. EP 13 780, ethoxylated fatty acid ethanolamides, as are described in European Patent No. EP 43 547, alkyl polyglycosides, in particular, sorbitan mono-, di- and triesters, as are described in European Patent No. EP 698 140 and fatty acid esters of polycarboxylic acids as are described in German Patent specification No. DE 2,822,891.

In the conditioning composition of the invention, softener can be present in amounts from 0.1 to 80% by weight, typically from 0.1 to 70% by weight, preferably from 0.2 to 60% by weight and in particular, from 0.5 to 40% by weight, in each case based on the total composition.

Conditioning compositions of the invention may preferably comprise one or more anionic surfactants, particularly those already described earlier on above.

Conditioning compositions of the invention may preferably comprise one or more nonionic surfactants, particularly those already described earlier on above.

Suitable further surfactants for all compositions of the invention, especially for the conditioning compositions, are what are called gemini surfactants. These are generally understood to be those compounds which have two hydrophilic groups and two hydrophobic groups per molecule. These groups are generally separated from one another by a so-called spacer. This spacer is usually a carbon chain which should be long enough for the hydrophilic groups to be adequately spaced so that they can function independently of one another. Such surfactants are generally characterized by an unusually low critical micelle concentration and the ability to greatly reduce the surface tension of water. In exceptional cases, however, the expression gemini surfactants is understood as meaning not only dimeric surfactants, but also trimeric surfactants.

Suitable gemini surfactants are, for example, sulfated hydroxy mixed ethers in accordance with German Patent Application No. DE-A-43 21 022 or dimer alcohol bis- and trimer alcohol tris-sulfates and ether sulfates in accordance with international patent application WO-A-96/23768. End-group-capped dimeric and trimeric mixed ethers according to German Patent Application No. DE-A-195 13 391 are characterized in particular, by their bi- and multifunctionality. Thus, said endgroup-capped surfactants have good wetting properties and are low-foam, meaning that they are suitable in particular, for use in machine washing and cleaning processes.

It is, however, also possible to use gemini-polyhydroxy fatty acid amides or poly-polyhydroxy fatty acid amides, as are described in the International Patent Application Nos. WO-A-95/19953, WO-A-95/19954 and WO-A-95/19955.

Further suitable surfactants are polyhydroxy fatty acid amides of the following formula,

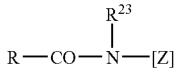

in which RCO is an aliphatic acyl radical having 6 to 22 carbon atoms, $R^{23}$ is hydrogen, an alkyl or hydroxyalkyl radical having 1 to 4 carbon atoms and [Z] is a linear or branched polyhydroxyalkyl radical having 3 to 10 carbon atoms and 3 to 10 hydroxyl groups. The polyhydroxy fatty acid amides are known substances which can usually be obtained by reductive amination of a reducing sugar with ammonia, an alkylamine or an alkanolamine and subsequent acylation with a fatty acid, a fatty acid alkyl ester or a fatty acid chloride.

The group of polyhydroxy fatty acid amides also includes compounds of the following formula,

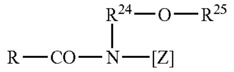

in which R is a linear or branched alkyl or alkenyl radical having 7 to 12 carbon atoms, $R^{24}$ is a linear, branched or cyclic alkyl radical or an aryl radical having 2 to 8 carbon atoms and $R^{25}$ is a linear, branched or cyclic alkyl radical or an aryl radical or an oxyalkyl radical having 1 to 8 carbon atoms, where $C_{1-4}$-alkyl or phenyl radicals are preferred and [Z] is a linear polyhydroxyalkyl radical whose alkyl chain is substituted by at least two hydroxyl groups, or alkoxylated, preferably ethoxylated or propoxylated, derivatives of these radicals.

[Z] is preferably obtained by reductive amination of a reduced sugar, for example glucose, fructose, maltose, lactose, galactose, mannose or xylose. The N-alkoxy- or N-aryloxy-substituted compounds can then be converted into the desired polyhydroxy fatty acid amides, for example, in accordance with the teaching in the international specification WO-A-95/07331, by reaction with fatty acid methyl esters in the presence of an alkoxide as catalyst.

The compositions of the invention preferably also comprise amphoteric surfactants. Alongside numerous mono- to trialkylated amine oxides, the betaines represent a significant class.

Betaines are known surfactants prepared predominantly by carboxyalkylation, preferably carboxymethylation, of aminic compounds. Preferably the starting materials are condensed with halocarboxylic acids or salts thereof, in particular, with sodium chloroacetate, one mole of salt being formed per mole of betaine. A further possibility is the addition reaction with unsaturated carboxylic acids, such as acrylic acid, for example. For the nomenclature and in particular, for differentiating between betaines and “real” amphosurfactants, reference is made to the article by U. Ploog in Seifen-Öle-Fette-Wachse, 108, 373 (1982). Other reviews on this subject are to be found in A. O’lennick et al. in HAPPI, Nov. 70 (1986), S. Holzman et al. in Tens. Surf. Det. 23, 309 (1986), R. Bibo et al. in Soap Cosm. Chem. Spec., Apr. 46 (1990) and P. Ellis et al. in Euro Cosm. 1, 14 (1994). Examples of suitable betaines are the carboxyalkylation products of secondary and in particular, tertiary amines that follow the formula (IX), (IX)

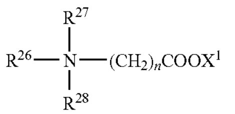

in which $R^{26}$ represents alkyl and/or alkenyl radicals having 6 to 22 carbon atoms, $R^{27}$ represents hydrogen or alkyl radicals having 1 to 4 carbon atoms, $R^{28}$ represents alkyl radicals having 1 to 4 carbon atoms, n represents numbers from 1 to 6, and $X^1$ represents an alkali metal and/or alkaline earth metal or ammonium. Typical examples are the carboxymethylation products of hexylmethylamine, hexyldimethylamine, octyldimethylamine, decyldimethylamine, dodecylmethylamine, dodecyldimethylamine, dodecylethylmethylamine, $C_{12/14}$-cocoalkyldimethylamine, myristyldimethylamine, cetyldimethylamine, stearyldimethylamine, stearylethylmethylamine, oleyldimethylamine, $C_{16/18}$-tallowalkyldimethylamine, and their technical mixtures.

Also suitable, furthermore, are carboxyalkylation products of amidoamines that follow the formula (X)

(X)

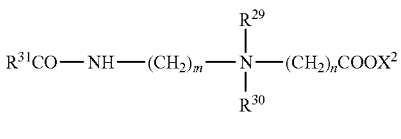

in which $R^{31}CO$ is an aliphatic acyl radical having 6 to 22 carbon atoms and 0 or 1 to 3 double bonds, m stands for numbers from 1 to 3, and $R^{29}$, $R^{30}$, n and $X^2$ have the definitions indicated above. Typical examples are reaction products of fatty acids with 6 to 22 carbon atoms, namely caproic acid, caprylic acid, capric acid, lauric acid, myristic acid, palmitic acid, palmoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and their technical mixtures, with N,N-dimethylaminoethylamine, N,N-dimethylaminopropylamine, N,N-diethylaminoethylamine, and N,N-diethylaminopropylamine, which are condensed with sodium chloroacetate. It is preferred to use a condensation product of $C_{8/18}$-cocoyl-N,N-dimethylaminopropylamide with sodium chloroacetate.

Also suitable as appropriate starting materials for the betaines which can be used for the purposes of the invention are imidazolines that follow the formula (XI)

(XI)

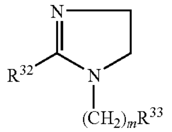

in which $R^{32}$ is an alkyl radical having 5 to 21 carbon atoms, $R^{33}$ is a hydroxyl group, a $OCOR^{32}$ or $NHCOR^{32}$ radical, and m is 2 or 3. These substances as well are known compounds, which can be obtained, for example, by cyclizing condensation of 1 or 2 mol of fatty acid with polyfunctional amines, such as aminoethylethanolamine (AEEA) or diethylenetriamine, for example. The corresponding carboxyalkylation products are mixtures of different open-chain betaines. Typical examples are condensation products of the above-mentioned fatty acids with AEEA, preferably imidazolines based on lauric acid or, again, $C_{12/14}$-coconut fatty acid, which are subsequently betainized with sodium chloroacetate.

In one preferred embodiment, the compositions of the invention are present in liquid form, for example, in the form of conditioning compositions or liquid washing compositions. To achieve a liquid consistency, the use both of liquid organic solvents, and also that of water may be appropriate. The compositions of the invention therefore optionally comprise solvents.

Solvents which may be used in the compositions of the invention originate, for example, from the group of mono- or polyhydric alcohols, alkanolamines or glycol ethers, provided they are miscible with water in the given concentration range. Preferably, the solvents are chosen from ethanol, n- or isopropanol, butanols, glycol, propanediol or butanediol, glycerol, diglycol, propyl or butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl or propyl ether, butoxypropoxypropanol (BPP), dipropylene glycol monomethyl or monoethyl ether, diisopropylene glycol monomethyl or monoethyl ether, methoxy, ethoxy or butoxy triglycol, 1-butoxyethoxy-2-propanol, 3-methyl-3-methoxybutanol, propylene glycol t-butyl ether, and mixtures of these solvents.

Some glycol ethers are available under the trade names Arcosolv® (Arco Chemical Co.) or Cellosolve®, Carbitol® or Propasol® (Union Carbide Corp.); these also include, for example, ButylCarbitol®, HexylCarbitol®, MethylCarbitol® and Carbitol® itself, (2-(2-ethoxy)ethoxy)ethanol. The choice of glycol ether can readily be made by the person skilled in the art on the basis of its volatility, solubility in water, its percentage by weight of the total dispersion and the like. Pyrrolidone solvents, such as N-alkylpyrrolidones, for example N-methyl-2-pyrrolidone or N—$C_8$-$C_{12}$-alkylpyrrolidone, or 2-pyrrolidone, can likewise be used. Also preferred as the sole solvents or as a constituent of a solvent mixture are glycerol derivatives, in particular, glycerol carbonate.

The alcohols which can preferably be used in the present invention as cosolvents include liquid polyethylene glycols, with a low molecular weight, for example polyethylene glycols with a molecular weight of 200, 300, 400 or 600. Further suitable cosolvents are other alcohols, for example (a) lower alcohols, such as ethanol, propanol, isopropanol and n-butanol, (b) ketones, such as acetone and methyl ethyl ketone, (c) $C_2$-$C_4$-polyols, such as a diol or a triol, for example ethylene glycol, propylene glycol, glycerol or mixtures thereof. From the class of diols, particular preference is given to 1,2-octanediol.

In one preferred embodiment, the composition of the invention comprises one or more solvents from the group consisting of $C_1$- to $C_4$-monoalcohols, $C_2$- to $C_6$-glycols, $C_3$- to $C_{12}$-glycol ethers and glycerol, in particular, ethanol. The $C_3$- to $C_{12}$-glycol ethers according to the invention comprise alkyl or alkenyl groups having fewer than 10 carbon atoms, preferably up to 8, in particular, up to 6, particularly preferably 1 to 4 and most preferably 2 to 3 carbon atoms.

Preferred $C_1$- to $C_4$-monoalcohols are ethanol, n-propanol, isopropanol and tert-butanol. Preferred $C_2$- to $C_6$-glycols are ethylene glycol, 1,2-propylene glycol, 1,3-propylene glycol, 1,5-pentanediol, neopentyl glycol and 1,6-hexanediol, in particular, ethylene glycol and 1,2-propylene glycol. Preferred $C_3$- to $C_{12}$-glycol ethers are di-, tri-, tetra- and pentaethylene glycol, di-, tri- and tetrapropylene glycol, propylene glycol monotertiary-butyl ether and propylene glycol monoethyl ether, and the solvents referred to according to INCI as butoxydiglycol, butoxyethanol, butoxyisopropanol, butoxypropanol, butyloctanol, ethoxydiglycol, ethoxyethanol, ethyl hexanediol, isobutoxypropanol, isopentyldiol, 3-methoxybutanol, methoxylethanol, methoxyisopropanol and methoxymethylbutanol.

The composition of the invention preferably may comprise one or more solvents in an amount of customarily up to 40% by weight, preferably 0.1 to 30% by weight, in particular, 2 to 20% by weight, more preferably 3 to 15% by weight, most preferably 5 to 12% by weight, for example 5.3 or 10.6% by weight, in each case based on the total composition.

In one preferred embodiment, the composition, particularly the conditioning composition, of the invention can optionally comprise one or more complexing agents.

Complexing agents (INCI Chelating Agents), also called sequestrants, are ingredients which are able to complex and deactivate metal ions in order to prevent, for example, their disadvantageous effects on the stability or the appearance of the composition, for example turbidity. On the one hand, it is important to complex the calcium and magnesium ions of water hardness which are incompatible with numerous ingredients. The complexation of the ions of heavy metals such as iron or copper delays the oxidative decomposition of the completed compositions.

Suitable complexing agents are, for example, the following complexing agents named in accordance with INCI, which are described in more detail in the International Cosmetic Ingredient Dictionary and Handbook: Aminotrimethylene Phosphonic Acid, Beta-Alanine Diacetic Acid, Calcium Disodium EDTA, Citric Acid, Cyclodextrin, Cyclohexanediamine Tetraacetic Acid, Diammonium Citrate, Diammonium EDTA, Diethylenetriamine Pentamethylene Phosphonic Acid, Dipotassium EDTA, Disodium Azacycloheptane Diphosphonate, Disodium EDTA, Disodium Pyrophosphate, EDTA, Etidronic Acid, Galactaric Acid, Gluconic Acid, Glucuronic Acid, HEDTA, Hydroxypropyl Cyclodextrin, Methyl Cyclodextrin, Pentapotassium Triphosphate, Pentasodium Aminotrimethylene Phosphonate, Pentasodium Ethylenediamine tetramethylene Phosphonate, Pentasodium Pentetate, Pentasodium Triphosphate, Pentetic Acid, Phytic Acid, Potassium Citrate, Potassium EDTMP, Potassium Gluconate, Potassium Polyphosphate, Potassium Trisphosphonomethylamine Oxide, Ribonic Acid, Sodium Chitosan Methylene Phosphonate, Sodium Citrate, Sodium Diethylenetriamine Pentamethylene Phosphonate, Sodium Dihydroxyethylglycinate, Sodium EDTMP, Sodium Gluceptate, Sodium Gluconate, Sodium Glycereth-1 Polyphosphate, Sodium Hexametaphosphate, Sodium Metaphosphate, Sodium Metasilicate, Sodium Phytate, Sodium Polydimethylglycinophenolsulfonate, Sodium Trimetaphosphate, TEA-EDTA, TEA-Polyphosphate, Tetrahydroxyethyl Ethylenediamine, Tetrahydroxypropyl Ethylenediamine, Tetrapotassium Etidronate, Tetrapotassium Pyrophosphate, Tetrasodium EDTA, Tetrasodium Etidronate, Tetrasodium Pyrophosphate, Tripotassium EDTA, Trisodium Dicarboxymethyl Alaninate, Trisodium EDTA, Trisodium HEDTA, Trisodium NTA and Trisodium Phosphate.

Preferred complexing agents are tertiary amines, in particular, tertiary alkanolamines (amino alcohols). The alkanolamines have both amino and also hydroxyl and/or ether groups as functional groups. Particularly preferred tertiary alkanolamines are triethanolamine and tetra-2-hydroxypropylethylenediamine (N,N,N',N'-tetrakis(2-hydroxypropyl) ethylenediamine). Particular preference is given to combinations of tertiary amines with zinc ricinoleate and one or more ethoxylated fatty alcohols as nonionic solubilizers and also, where appropriate, solvents are described in DE 40 14 055 C2 (Grillo-Werke), to which reference is made in this respect and the content of which is included in this application.

A particularly preferred complexing agent is etidronic acid (1-hydroxyethylidene-1,1-diphosphonic acid, 1-hydroxyethyane-1,1-diphosphonic acid, HEDP, acetophosphonic acid, INCI Etidronic Acid) including its salts. In a preferred embodiment, the composition according to the invention accordingly comprises, as complexing agent, etidronic acid and/or one or more of its salts.

In a particular embodiment, the composition according to the invention comprises a complexing agent combination of one or more tertiary amines and one or more further complexing agents, preferably one or more complexing agent acids or salts thereof, in particular, of triethanolamine and/or tetra-2-hydroxypropylethylenediamine and etidronic acid and/or one or more of its salts.

The composition, especially conditioning composition, of the invention comprises complexing agents advantageously in an amount of usually 0 to 20% by weight, preferably 0.1 to 15% by weight, in particular, 0.5 to 10% by weight, particularly preferably 1 to 8% by weight, most preferably 1.5 to 6% by weight.

In a further embodiment, the composition, especially conditioning composition, of the invention optionally comprises one or more viscosity regulators that act preferably as thickeners.

The viscosity of the compositions can be measured using customary standard methods (for example Brookfield viscometer RVD-VII at 20 rpm and 20° C., spindle 3) and is preferably in the range from 10 to 5,000 mPas. Preferred liquid to gel-like agents have viscosities of from 20 to 4,000 mPas, particular preference being given to values between 40 and 2,000 mPas.

Suitable thickeners are inorganic or polymeric organic compounds. It is also possible to use mixtures of two or more thickeners.

The inorganic thickeners include, for example, polysilicic acids, clay minerals such as montmorillonites, zeolites, silicas, aluminum silicates, phyllosilicates and bentonites.

The organic thickeners originate from the groups of natural polymers, modified natural polymers and completely synthetic polymers.

Polymers originating in nature which are used as thickeners are, for example, xanthan, agar-agar, carrageen, tragacanth, gum arabic, alginates, pectins, polyoses, guar flour, gellan gum, carob seed flour, starch, dextrins, gelatins and casein.

Modified natural substances originate primarily from the group of modified starches and celluloses, examples which may be mentioned here being carboxymethylcellulose and other cellulose ethers, hydroxyethylcellulose and hydroxypropylcellulose, highly etherified methylhydroxyethylcellulose, and carob flour ether.

A large group of thickeners which is used widely in very diverse fields of application are the completely synthetic polymers, such as polyacrylic and polymethacrylic compounds which may be crosslinked or uncrosslinked and optionally cationically modified, vinyl polymers, polycarboxylic acids, polyethers, activated polyamide derivatives, castor oil derivatives, polyimines, polyamides and polyurethanes. Examples of suitable polymers are acrylic resins, ethyl acrylate-acrylamide copolymers, acrylic ester-methacrylic ester copolymers, ethyl acrylate-acrylic acid-methacrylic acid copolymers, N-methylolmethacrylamide, maleic anhydride-methyl vinyl ether copolymers, polyether-polyol copolymers, and butadiene-styrene copolymers.

Further suitable thickeners are derivatives of organic acids and alkoxide adducts thereof, for example aryl polyglycol ethers, carboxylated nonylphenol ethoxylate derivatives, sodium alginate, diglycerol monoisostearate, nonionogenic ethylene oxide adducts, coconut fatty acid diethanolamide, isododecenylsuccinic anhydride, and galactomannan. Thickeners from said classes of substance are commercially available and are offered, for example, under the trade names Acusol®-820 (methacrylic acid (stearyl alcohol-20-EO) ester-acrylic acid copolymer, 30% strength in water, Rohm & Haas), Dapral®-GT-282-S (alkyl polyglycol ether, Akzo), Deuterol®-Polymer-11 (dicarboxylic acid copolymer, Schöner GmbH), Deuteron®-XG (anionic heteropolysaccharide based on β-D-glucose, D-manose, D-glucuronic acid, Schöner GmbH), Deuteron®-XN (nonionogenic polysaccharide, Schöner GmbH), Dicrylan®-Verdicker-O (ethylene oxide adduct, 50% strength in water/isopropanol, Pfersse Chemie), EMA®-81 and EMA®-91 (ethylene-maleic anhydride copolymer, Monsanto), Verdicker-QR-1001 (polyurethane emulsion, 19-21% strength in water/diglycol ether, Rohm & Haas), Mirox®-AM (anionic acrylic acid-acrylic ester copolymer dispersion, 25% strength in water, Stockhausen), SER-AD-FX-1100 (hydrophobic urethane polymer, Servo Delden), Shellflo®-S (high molecular weight polysaccharide, stabilized with formaldehyde, Shell), Shellflo®-XA (xanthan biopolymer, stabilized with formaldehyde, Shell), Kelzan, Keltrol T (Kelco).

In a further preferred embodiment, the composition, especially conditioning composition, of the invention optionally comprises one or more enzymes.

Suitable enzymes are, in particular, those from the classes of hydrolases, such as the proteases, esterases, lipases or lipolytic enzymes, amylases, cellulases or other glycosylhydrolases and mixtures of said enzymes. All of these hydrolases contribute, during laundering, to the removal of stains such as proteinaceous, grease-containing or starchy stains and graying. Cellulases and other glycosylhydrolases can, moreover, contribute to color retention and to an increase in the softness of the textile by removing pilling and microfibrils. For bleaching and for inhibiting color transfer it is also possible to use oxireductases.

Particularly highly suitable are enzymatic active ingredients obtained from bacterial strains or fungi such as *Bacillus subtilis, Bacillus licheniformis, Streptomyceus griseus* and *Humicola insolens*. Preference is given to using proteases of the subtilisin type and in particular, proteases obtained from *Bacillus lentus*. In this connection, enzyme mixtures, for example of protease and amylase or protease and lipase or lipolytic enzymes or protease and cellulase or of cellulase and lipase or lipolytic enzymes or of protease, amylase and lipase or lipolytic enzymes or protease, lipase or lipolytic enzymes and cellulase, but in particular, protease and/or lipase-containing mixtures or mixtures with lipolytic enzymes are of particular interest. Examples of such lipolytic enzymes are the known cutinases. Peroxidases or oxidases have also proven to be suitable in some cases. Suitable amylases include, in particular, α-amylases, isoamylases, pullulanases and pectinases. As cellulases, preference is given to using cellobiohydrolases, endoglucanases and β-glucosidases, which are also called cellobiases, or mixtures thereof. Since various types of cellulase differ in their CMCase and avicelase activities, the cellulases can be mixed in a targeted manner to achieve the desired activities.

The enzymes can be embedded as shaped bodies adsorbed or coated onto carrier substances in order to protect them against premature decomposition. The proportion of the enzymes, enzyme mixtures or enzyme granules can, for example, be about 0.1 to 5% by weight, preferably 0.12 to about 2% by weight, based on the overall composition.

The compositions of the invention, such as, in particular, detergents, care products or conditioning compositions, may optionally comprise bleaches. Among the compounds serving as bleaches which produce $H_2O_2$ in water, sodium percarbonate, sodium perborate tetrahydrate and sodium perborate monohydrate are of particular importance. Further bleaches which can be used are, for example, peroxopyrophosphates, citrate perhydrates, and $H_2O_2$-producing peracidic salts or peracids, such as persulfates or persulfuric acid. It is also possible to use the urea peroxohydrate percarbamide, which can be described by the formula $H_2N—CO—NH_2.—H_2O_2$. Particularly when the agents are used for the cleaning of hard surfaces, for example for machine dishwashing, they can, if desired, also comprise bleaches from the group of organic bleaches, although their use is in principle also possible for agents for textile washing. Typical organic bleaches are the diacyl peroxides, such as, for example, dibenzoyl peroxide. Further typical organic bleaches are the peroxy acids, particular examples being the alkylperoxy acids and the arylperoxy acids. Preferred representatives are peroxybenzoic acid and its ring-substituted derivatives, such as alkylperoxybenzoic acids, but also peroxy-α-naphthoic acid and magnesium monoperphthalate, the aliphatic or substituted aliphatic peroxy acids, such as peroxylauric acid, peroxystearic acid, ϵ-phthalimidoperoxycaproic acid (phthalimidoperoxyhexanoic acid, PAP), o-carboxybenzamidoperoxycaproic acid, N-nonenylamidoperadipic acid and N-nonenylamidopersuccinates, and aliphatic and araliphatic peroxydicarboxylic acids, such as 1,12-diperoxycarboxylic acid, 1,9-diperoxyazelaic acid, diperoxysebacic acid, diperoxybrassylic acid, the diperoxyphthalic acids, 2-decyldiperoxybutane-1,4-dioic acid, N,N-terephthaloyl-di(6-aminopercaproic acid) can be used.

The bleaches can preferably be coated in order to protect them against premature decomposition.

Dyes can be used in the composition of the invention, the amount of one or more dyes being chosen to be so low that no visible residues remain following use of the composition. The composition of the invention is preferably free from dyes.

The composition of the invention can preferably have one or more antimicrobial active ingredients or preservatives in an amount of usually 0.0001 to 3% by weight, preferably 0.0001 to 2% by weight, in particular, 0.0002 to 1% by weight, particularly preferably 0.0002 to 0.2% by weight, most preferably 0.0003 to 0.1% by weight.

Antimicrobial active ingredients or preservatives are differentiated, depending on the antimicrobial spectrum and mechanism of activity, between bacteriostats and bacteriocides, fungistats and fungicides etc. Important substances from these groups are, for example, benzalkonium chlorides, alkylarylsulfonates, halophenols and phenol mercuriacetate. For the purposes of the teaching according to the invention, the terms antimicrobial effect and antimicrobial active ingredient have the standard specialist meanings which are given, for example, by K. H. Wallhäußer in "Praxis der Sterilisation, Desinfektion—Konservierung: Keim-identifizierung—Betriebshygiene" [Practice of Sterilization, Disinfection—Preservation: Microbial Identification—Operational Hygiene] (5th edition—Stuttgart; New York: Thieme, 1995), where all of the substances with an antimicrobial effect described therein can be used. Suitable antimicrobial active ingredients are preferably chosen from the groups of alcohols, amines, aldehydes, antimicrobial acids or salts thereof, carboxylic esters, acid amides, phenols, phenol derivatives, diphenyls, diphenylalkanes, urea derivatives, oxygen-, nitrogen-acetals and formals, benzamidines, isothiazolines, phthalimide derivatives, pyridine derivatives, antimicrobial surface-active compounds, guanidines, antimicrobial amphoteric compounds, quinolines, 1,2-dibromo-2,4-dicyanobutane, iodo-2-propylbutyl carbamate, iodine, iodophores, peroxo compounds, halogen compounds and any mixtures of the above.

Here, the antimicrobial active ingredient can be chosen from ethanol, n-propanol, isopropanol, 1,3-butanediol, phenoxyethanol, 1,2-propylene glycol, glycerol, undecylenic acid, benzoic acid, salicylic acid, dihydracetic acid, o-phenylphenol, N-methylmorpholinium acetonitrile (MMA), 2-benzyl-4-chlorophenol, 2,2'-methylenebis(6-bromo-4-chlorophenol), 4,4'-dichloro-2'-hydroxydiphenyl ether (dichlosan), 2,4,4'-trichloro-2'-hydroxydiphenyl ether (trichlosan), chlorhexidine, N-(4-chlorophenyl)-N-(3,4-dichlorophenyl)urea, N,N'-(1,10-decanediyldi-1-pyridinyl-4-ylidene)bis(1-octanamine) dihydrochloride, N,N'-bis-(4-chlorophenyl)-3,12-diimino-2,4,11,13-tetraazatetradecanediimide amide, glucoprotamines, antimicrobial surface-active quaternary compounds, guanidines, including the bi- and polyguanidines, such as, for example, 1,6-bis(2-ethylhexylbiguamidohexane) dihydrochloride, 1,6-di($N_1$,$N_1$'-phenyldiguamido-$N_5$,$N_5$')hexane tetrahydrochloride, 1,6-di($N_1$,$N_1$'-phenyl-$N_1$,$N_1$'-methyldiguamido-$N_5$,$N_5$')hexane dihydrochloride, 1,6-di($N_1$,$N_1$'-o-chlorophenyldiguamido-$N_5$,$N_5$')hexane dihydrochloride, 1,6-di($N_1$,$N_1$'-2,6-dichlorophenyldiguamido-$N_5$,$N_5$')hexane dihydrochloride, 1,6-di[$N_1$,$N_1$'-β-(p-methoxyphenyl)-diguamido-$N_5$,$N_5$']hexane dihydrochloride, 1,6-di($N_1$,$N_1$'-α-methyl-β-phenyldiguamido-$N_5$,$N_5$')hexane dihydrochloride, 1,6-di($N_1$,$N_1$'-p-nitrophenyldiguamido-$N_5$,$N_5$')hexane dihydrochloride, ω:ω-di($N_1$,$N_1$'-phenyldiguamido-$N_5$,$N_5$')-di-n-propyl ether dihydrochloride, ω:ω-di($N_1$, $N_1$'-p-chlorophenyldiguamido-$N_5$,$N_5$')-di-n-propyl ether tetrahydrochloride, 1,6-di($N_1$, $N_1$'-2,4-dichlorophenyldiguamido-$N_5$, $N_5$')hexane tetrahydrochloride, 1,6-di($N_1$, $N_1$'-p-methylphenyldiguamido-$N_5$,$N_5$')hexane dihydrochloride, 1,6-di($N_1$,$N_1$'-2,4,5-trichlorophenyldiguamido-$N_5$,$N_5$')hexane tetrahydrochloride, 1,6-di[$N_1$,$N_1$'-α-(p-chlorophenyl)ethyldiguamido-$N_5$, $N_5$']hexane dihydrochloride, ω:ω-di($N_1$, $N_1$'-p-chlorophenyldiguamido-$N_5$, $N_5$')-m-xylene dihydrochloride, 1,12-di($N_1$, $N_1$'-p-chlorophenyldiguamido-$N_5$, $N_5$') dodecane dihydrochloride, 1,10-di($N_1$, $N_1$'-phenyldiguamido-$N_5$, $N_5$')decane tetrahydrochloride, 1,12-di($N_1$,$N_1$'-phenyldiguamido-$N_5$,$N_5$')dodecane tetrahydrochloride, 1,6-di($N_1$,$N_1$'-o-chlorophenyldiguamido-$N_5$,$N_5$')hexane dihydrochloride, 1,6-di($N_1$,$N_1$'-o-chlorophenyldiguamido-$N_5$,$N_5$')hexane tetrahydrochloride, ethylenebis(1-tolylbiguanide), ethylenebis(p-tolylbiguanide), ethylenebis(3,5-dimethylphenylbiguanide), ethylenebis(p-tert-amylphenylbiguanide), ethylenebis(nonylphenylbiguanide), ethylenebis(phenylbiguanide), ethylenebis(N-butylphenylbiguanide), ethylenebis(2,5-diethoxyphenylbiguanide), ethylenebis(2,4-dimethylphenylbiguanide), ethylenebis(o-diphenylbiguanide), ethylenebis(mixed amyl-naphthylbiguanide), N-butylethylenebis(phenylbiguanide), trimethylenebis(o-tolylbiguanide), N-butyltrimethylebis (phenylbiguanide) and the corresponding salts, such as acetates, gluconates, hydrochlorides, hydrobromides, citrates, bisulfites, fluorides, polymaleates, N-cocoalkyl sarcosinates, phosphites, hypophosphites, perfluorooctanoates, silicates, sorbates, salicylates, maleates, tartrates, fumarates, ethylenediaminetetraacetates, iminodiacetates, cinnamates, thiocyanates, arginates, pyromellitates, tetracarboxybutyrates, benzoates, glutarates, monofluorophosphates, perfluoropropionates and any mixtures thereof. Also suitable are halogenated xylol and cresol derivatives, such as p-chlorometacresol or p-chlorometaxylol, and natural antimicrobial active ingredients of vegetable origin (e.g., from spices or herbs) animal origin, or microbial origin. Preference may be given to using antimicrobially active surface-active quaternary compounds, a natural antimicrobial active ingredient of vegetable origin and/or a natural antimicrobial active ingredient of animal origin, most preferably at least one natural antimicrobial active ingredient of vegetable origin from the group which includes caffeine, theobromine and theophylline and essential oils such as eugenol, thymol and geraniol, and/or at least one natural antimicrobial active ingredient of animal origin from the group which includes enzymes such as milk protein, lysozyme and lactoperoxidase, and/or at least one antimicrobially active surface-active quaternary compound having an ammonium, sulfonium, phosphonium, iodonium or arsonium group, peroxo compounds and chlorine compounds. Substances of microbial origin, so called bacteriocines, can also be used. Glycine, glycine derivatives, formaldehyde, compounds which readily release formaldehyde, formic acid and peroxides are preferably used.

The quaternary ammonium compounds (QACs) suitable as antimicrobial active ingredients have already been described above. Particularly suitable for example is benzalkonium chloride.

Benzalkonium halides and/or substituted benzalkonium halides are, for example, commercially available as Barquat® ex Lonza, Marquat® ex Mason, Variquat® ex Witco/Sherex and Hyamine® ex Lonza, and Bardac® ex Lonza. Further commercially available antimicrobial active ingredients are N-(3-chloroallyl)hexaminium chloride such as Dowicide® and Dowicil® ex Dow, benzethonium chloride such as Hyamine® 1622 ex Rohm & Haas, methylbenzethonium chloride such as Hyamine® 10× ex Rohm & Haas, cetylpyridinium chloride such as cepacol chloride ex Merrell Labs.

The compositions of the invention, such as, in particular, detergents, care products or conditioning compositions, may where appropriate further include ironing assistants for improving the water absorption capacity, the rewettability of the treated textiles, and for facilitating the ironing of the treated textiles. Silicone derivatives, for example, may be used in the formulations. These additionally improve the rinse-out behavior of the detergent formulations, by virtue of their foam-inhibiting properties. Examples of preferred silicone derivatives are polydialkylsiloxanes or alkylarylsiloxanes in which the alkyl groups have one to five C atoms and are wholly or partly fluorinated. Preferred silicones are polydimethylsiloxanes, which where appropriate may be derivatized and are then amino-functional or quaternized, or contain Si—OH, Si—H and/or Si—Cl bonds. The viscosities of the preferred silicones at 25° C. are situated in the range between 100 and 100,000 mPas, and the silicones can be used in amounts between 0.2% and 5% by weight, based on the composition as a whole.

The compositions of the invention, especially conditioning compositions, can be obtained by all known techniques familiar to the skilled worker. For example, the compositions can be obtained directly from their raw materials by mixing, where appropriate with the use of high-shear mixing apparatus. For liquid formulations, especially conditioning compositions, it is advisable to melt any softener components present and then to disperse the melt in a solvent, preferably water. The inventively useful polymerizable betaine esters of the formula (I) or polymers preparable from them in accordance with the invention can be integrated into the conditioning compositions by means of simple mixing.

The conditioning compositions preferably take the form of fabric softeners. In that case they are typically introduced in the rinse cycle of an automatic washing machine. The attractiveness of the inventively useful polymerizable betaine esters of the general formula (I) and/or the polymeric betaine esters, which in the case of the homopolymers are prepared from the monomeric polymerizable betaine esters of the general formula (I) and/or in the case of the copolymers are prepared from polymerizable betaine esters of the general formula (I) and suitable comonomers of the general formula (II), for textile surfaces or fabrics means that the treated textiles not only have a better soft hand but also, additionally, leave an extremely long-lasting fragrance sensation on the textiles (when using fragrance alcohol-esterified inventively useful polymerizable betaine esters of the general formula (I) and/or the polymeric betaine esters, which in the case of the homopolymers are prepared from the monomeric polymerizable betaine esters of the general formula (I) and/or in the case of the copolymers are prepared from polymerizable betaine esters of the general formula (I) and suitable comonomers of the general formula (II).

The invention further provides a substrate, in particular, a conditioning substrate, which is impregnated and/or coated with a composition of the invention, preferably a conditioning composition, which thus, in addition to other constituents, comprises the fragrance preparation of the invention.

Conditioning substrates of the invention find their use in particular, in textile treatment and especially in textile drying processes. The substrate material consists preferably of porous, flat cloths. They can consist of a fibrous or cellular flexible material which has adequate thermal stability for use in the dryer and which can retain adequate amounts of an impregnation or coating agent in order to effectively condition substances without significant leakage or bleeding of the agent taking place during storage. These cloths include cloths made of woven and non-woven synthetic and natural fibers, felt, paper or foam material, such as hydrophilic polyurethane foam.

Preference is given here to using conventional cloths made of non-woven material (nonwovens). Nonwovens are generally defined as adhesively bonded fibrous products which have a mat or layered fiber structure, or those which include fiber mats in which the fibers are distributed randomly or in statistical arrangement. The fibers may be natural, such as wool, silk, jute, hemp, cotton, linen, sisal or ramie; or synthetic, such as rayon, cellulose ester, polyvinyl derivatives, polyolefins, polyamides or polyesters. In general, any fiber diameter or titer is suitable for the present invention. The non-woven materials used here have a tendency, due to the random or statistical arrangement of fibers in the non-woven material, to impart excellent strength in all directions, not to tear or disintegrate when they are used, for example, in a customary domestic laundry dryer. Examples of non-woven materials which are suitable as substrates in the present invention are known, for example from WO 93/23603. Preferred porous and flat cleaning cloths consist of one or different fiber materials, in particular, of cotton, finished cotton, polyamide, polyester or mixtures thereof. Preferably, the cleaning substrates in cloth form have an area of from 10 to 5,000 $cm^2$, preferably from 50 to 2,000 $cm^2$, in particular, from 100 to 1,500 $cm^2$ and particularly preferably from 200 to 1,000 $cm^2$. The grammage of the material here is usually between 20 and 1,000 $g/m^2$, preferably from 30 to 500 $g/m^2$, and in particular, from 50 to 150 $g/m^2$. Conditioning substrates can be obtained by soaking or impregnating or else by melting the inventive compositions or conditioning compositions onto a substrate.

The invention further provides for the use of a conditioning composition or of a conditioning substrate of the invention in a textile conditioning method, such as a rinse cycle, a textile drying method and textile dry-cleaning method or textile freshen-up method, for example.

Preferred compositions of the invention are liquid detergents preferably comprising surfactant(s) and also further typical ingredients of detergents. By way of example it is possible for liquid detergents suitable in accordance with the invention to comprise as a thickening system, based in each case on the overall composition, a) 0.1% to 5% by weight of a polymeric thickener, b) 0.5% to 7% by weight of a boron compound, and c) 1% to 8% by weight of a complexing agent. Liquid laundry detergents are described, for example, in WO 99/27051, to which reference is made herein in its entirety. In the context of the present invention, preference is given to aqueous liquid laundry detergents of relatively high viscosity whose surfactant content is above 35% by weight.

Suitable thickeners, also called swelling agents, such as alginates or agar-agar, for example, have already been described earlier on above. Preferred aqueous liquid laundry detergents contain as their thickening system 0.2% to 4%, preferably 0.3% to 3%, and in particular, 0.4% to 1.5% by weight of a polysaccharide.

A polymeric thickener whose use is preferred is xanthan, a microbial anionic heteropolysaccharide which is produced by *Xanthomonas campestris* and certain other species under aerobic conditions and has a molar mass of 2 to 15 million daltons. Xanthan is formed from a chain with β-1,4-attached glucose (cellulose) with side chains. The structure of the subgroups is composed of glucose, mannose, glucoronic acid, acetate, and pyruvate, the number of pyruvate units determining the viscosity of the xanthan.

Liquid laundry detergents of the invention may preferably include a boron compound, which is used in amounts of 0.5% to 7% by weight. Examples of boron compounds which can be used for the purposes of the present invention are boric acid, boron oxide, alkali metal borates such as ammonium, sodium, and potassium ortho-, meta-, and pyroborates, borax in its different hydration states, and polyborates, such as alkali metal pentaborates, for example.

Organic boron compounds as well, such as esters of boronic acid, can be employed.

Preferred liquid laundry detergents contain 0.5% to 4%, preferably 0.75% to 3%, and in particular, 1% to 2% by weight of boric acid and/or sodium tetraborate.

It is also possible for liquid laundry detergents of the invention to contain 1% to 8% by weight of a complexing agent. Particularly preferred liquid laundry detergents contain in this case citric acid or sodium citrate, preference being given to liquid laundry detergents containing 2.0% to 7.5%, preferably 3.0% to 6.0%, and in particular, 4.0% to 5.0% by weight of sodium citrate.

Besides the constituents of the thickening system, the liquid laundry detergents of the invention comprise surfactant(s), use being made of anionic, nonionic, cationic and/or amphoteric surfactants. Preference is given from a performance standpoint to mixtures of anionic and nonionic surfactants, it being possible with preference for the fraction of the nonionic surfactants to be greater than the fraction of anionic surfactants. It is likewise possible to use sugars and/or sugar derivatives such as alkylpolyglucosides or cyclodextrins, for example.

The invention additionally provides for the use of a fragrance preparation of the invention for producing a citrus odor.

The citrus odor may be produced directly and/or indirectly. If, for example, the fragrance preparation is added to a laundry detergent, a citrus fragrance is emitted directly from the detergent. In this way, therefore, a citrus odor is produced directly in the detergent. If, for example, this laundry detergent, fragranced in this way, is used for laundering, in an automatic washing machine, for example, then the washed laundry also emits a citrus odor. In this way, therefore, a citrus odor is produced indirectly on the laundry.

The fragrance transfer agent, according to one preferred embodiment, in the context of the inventive use for producing a citrus odor, is a composition, a sprayable composition, in particular, a product made up of a sprayable composition and a spray dispenser, a textile treatment composition, in particular, a textile treatment composition with anti-crease compounds, a cleaning cloth, an ironing assistant, a laundry detergent, a cleaning product for hard and/or soft surfaces, a stainless steel cleaner, a household cleaner, an oven cleaner, a care product, a laundering care product, a laundry care product, a room fragrancer, a hair treatment composition, a hair colorant, a conditioning composition, a fabric softener, a conditioning substrate, a pharmaceutical, a crop protection product, a foodstuff, a cosmetic, a fertilizer, a building material, an adhesive, a bleach, a disinfectant, a fragrancing product and/or a precursor of the aforementioned products.

A further preferred embodiment lies in the use of a fragrance preparation of the invention for treating textiles, where the citrus fragrance is released preferably in a laundry dryer, in a washing machine, during ironing and/or during pressing of textiles.

A further preferred embodiment lies in the use of at least one encapsulant and/or release retardant for releasing and/or transferring a fragrance preparation of the invention onto a product, the release taking place as a consequence of a chemical reaction, under temperature, pH, pressure and/or solubility control.

A further preferred embodiment lies in the use of at least one encapsulant and/or release retardant, the encapsulant being based on a polymeric, waxlike and/or resinous compound.

The invention further provides for the use of a fragrance preparation of the invention for substituting geranonitrile. The substitution of the geranonitrile by the fragrance preparation of the invention may be partial or complete. The substitution of geranonitrile relates preferably to typical product applications, such as, for example, laundry detergents and cleaning products, care products, textile treatment products, ironing assistants, cleaning cloths, especially for hard and/or soft surfaces, household cleaners, wash care products, laundry care products, room fragrancers, air fresheners, conditioning compositions, colorants, fabric softeners, conditioning substrates, pharmaceuticals, crop protection products, polishes, foodstuffs, cosmetics, fertilizers, building materials, adhesives, bleaches, decalcifiers, autocare products, floorcare products, ovencare products, leathercare products, furniture care products, scouring products, disinfectants, fragrancers, mold remover products and/or precursors of the aforementioned products. In all of these compositions, and in further, comparable compositions, it is advantageously possible to replace some or all of any geranonitrile present by the fragrance preparation of the invention. This means that in the perfuming of such products, such as detergents, for example, it is possible, advantageously, to dispense partly or wholly with the incorporation of geranonitrile, since the fragrance preparation of the invention is able to stand in its stead as an equivalent replacement.

EXAMPLES

Example 1

The following formula represents a nonlimiting example of a fragrance preparation of the invention, referred to below as "FP 1":

| Odorants | Parts by weight |
|---|---|
| 2,4,6-Trimethyl-4-phenyl-1,3-dioxane | 50 |
| 2-Benzyl-2-methyl-3-butenenitrile | 50 |
| 3,7-Dimethyl-6-octenenitrile | 500 |
| Citronellyl acetate | 100 |
| 2,4-Dimethyl-4-phenyltetrahydrofuran | 10 |
| 1,1-Dimethoxy-3,7-dimethyl-2,6-octadiene | 30 |
| 2-(2-Methyl-3-phenyl)propyl acetate | 20 |
| 9-Decen-1-ol | 10 |
| cis-, trans-3-Methyl-5-phenyl-2-pentenenitrile | 100 |
| Undecanal, isomer mixture | 10 |
| 2-Butyl-4,6-dimethyldihydropyran | 10 |
| Ethylmethoxynorbonane (isomer mixture) | 10 |
| Further odorants and dipropylene glycol | 100 |
| Total | 1,000 |

Example 2

Three liquid conditioning compositions were produced. They had the same formula, as indicated below, but they differ in the perfume component. This component contained in the case of conditioner a) 40% by weight FP 1, in the case of conditioner b) 40% by weight of geranonitrile, and in the case of conditioner c) 40% by weight of 3,7-dimethyloct-6-enenitrile, based in each case on the whole perfume present.

Liquid Conditioning Composition:

| | % by weight |
|---|---|
| Rewoquat WE 18[a] | 22.5 |
| Silicone oil[b] | 5 |
| $MgCl_2 \times 6H_2O$ | 0.5 |

-continued

| | % by weight |
|---|---|
| Perfume | 1.6 |
| Water, demineralized | ad 100 |

[a]N-methyl-N-(2-hydroxyethyl)-N,N-(ditallow-acycl-oxyethyl)ammonium methosulfate ex Degussa
[b]Silicone oil ex Ciba The formula was produced by melting the ester quat in water. The melted ester quat was then stirred with a highly dispersing apparatus and the remaining components were added. The perfume was added after the mixture had cooled to below 30° C.

Cotton laundry (12 white hand towels) were then treated with these conditioning compositions in a washing machine. Total amount of conditioner: 36 g in each case; washing machine type Miele Novotronic W135; standard rinse cycle at rinsing temperature: 20° C. without prior wash cycle.

Taking part in the comparative tests were in each case 12 testers (non-experts in perfumery), who assessed the fragrance, based in each case on the odor of the product as such and also of the odor of the laundry in both the damp and dry conditions. By damp condition is meant that the damp laundry was removed from the drum after spinning and its fragrance was assessed. The laundry was subsequently dried on the line. The fragrance of the dry laundry was assessed after two days, the individual items of dry laundry having been stored carefully separated from one another in open plastic bags. The specimens were assessed in a blind comparison—that is, the testers did not know that the conditioning compositions contained different perfumes.

Result.

With Regard to the Pure Conditioning Compositions.

Eleven testers expressed the opinion that, in terms of odor, the pure conditioners a) and b) were indistinguishable. Only one tester announced an ability to distinguish them. Eight testers were of the view that conditioners c) were different from compositions a) and b). Four testers were unable to find any difference and declared all of the compositions to be of equal odor.

With Regard to the Damp Laundry.

Eleven testers expressed the opinion that, in terms of odor, the loads of damp laundry washed with conditioners a) and b) were indistinguishable. Of these eleven testers, however, eight testers stated that, although the laundry washed with a) smelled the same, the fragrance sensation was nevertheless more intense in the case of a). Seven testers were of the view that the laundry washed with conditioner c) was different in terms of odor from a) and b). The laundry washed with a) and b), moreover, was said to have a fresher and more intense smell. Five testers were unable to ascertain any difference and declared all of the compositions to smell the same. Of these five, four regarding c) that although it smelled the same, had a less intense smell.

With Regard to the Dry Laundry.

All of the testers expressed the opinion that, in terms of odor, the loads of dry laundry washed with conditioners a) and b) were indistinguishable. Of these twelve, however, ten testers stated that, although the laundry washed with a) smelled the same, the fragrance sensation was nevertheless significantly weaker in the case of b). Six testers were of the view that the laundry washed with conditioner c) was different in terms of odor from a) and b). The laundry washed with a) and b), moreover, was said to have a fresher smell. The laundry washed with c), moreover, was said to have a much weaker smell. Six testers were unable to ascertain any difference and declared all of the compositions to smell the same. Of these six, four declared regarding c) that although it smelled the same, had a less intense smell.

Examples 3 to 5

Liquid Cleaners.

Three liquid cleaners were produced, with the formula given below. They were identical except for the perfume component. Liquid cleaner a) contained 40% by weight of FP1, liquid cleaner b) 40% by weight of geranonitrile, and liquid cleaner c) 40% by weight of 3,7-dimethyloct-6-enenitrile, based in each case on the total perfume present.

Liquid Cleaner

| Raw material | Amount in % by weight |
|---|---|
| C12-18 fatty acid, Na salt | 0.7 |
| C10-13 alkylbenzenesulfonate | 6.4 |
| Sodium citrate | 1.5 |
| Sodium carbonate | 3.0 |
| Ethanol | 2.1 |
| Cumene sulfate, Na | 1.5 |
| C12-18 fatty alcohol + 7EO | 1.5 |
| C8 fatty alcohol sulfate, Na salt | 1.5 |
| Perfume | 0.7 |
| Water | ad 100 |

The liquid cleaners were assessed in odor terms by 13 testers (nonexperts from a perfume standpoint), based in each case on the odor of the product as such and also on the odor of a wet wipe. 30 ml of each of the liquid cleaners was introduced into a bucket of water (contents: 3 l water, 20° C.) and dispersed therein. A cotton wipe was placed into this mixture for 30 seconds and then wrung out thoroughly by hand. A wet wipe thus treated was then assessed for odor.

Result with Regard to the Liquid Cleaner.

Twelve testers expressed the opinion that, in terms of odor, liquid cleaners a) and b) were indistinguishable. Eight testers were of the view that conditioner c) differed from compositions a) and b). Five testers were unable to ascertain any difference and declared all the compositions to be of equal odor.

Result with Regard to the Wet Wipe.

Thirteen testers expressed the opinion that the wet wipes resulting from liquid cleaners a) and b) were indistinguishable in terms of odor. Seven testers were of the view, however, that version c) was different from versions a) and b). Moreover, version c) had a less fresh smell. Six testers were unable to ascertain any difference and declared all the wipes to be of equal odor. Of these six, three explained that c), although smelling the same, had a less intense smell.

Examples 6 to 8

Three liquid laundry detergents were produced, with the formula given below. They were identical except for the perfume component. Liquid laundry detergent a) contained 40% by weight of FP1, detergent b) 40% by weight of geranonitrile, and detergent c) 40% by weight of 3,7-dimethyloct-6-enenitrile, based in each case on the total perfume present.

Liquid Laundry Detergents. Examples 6 to 8.

| Raw material | Amount in % by weight |
|---|---|
| C12-14 fatty acid | 8.8 |
| C12-18 fatty alcohol + 7EO | 24.0 |
| Akylpolyglucoside | 2.0 |
| C12-14-2EO sulfate | 5.0 |
| C16-18 fatty acid | 6.8 |
| NaOH 50% | 3.0 |
| Citric acid × 1H2O | 1.0 |
| Glycerol 99.5% | 7.5 |
| Ethanol | 1.0 |
| Silicone oil | 0.3 |
| Polyvinylpyrrolidone | 0.5 |
| 1-Hydroxyethylidene bis-phosphonate - 4Na | 0.5 |
| Perfume | 1.0 |
| Water | ad 100 |

These liquid laundry detergents were then used to treat cotton laundry (14 white hand towels) in a washing machine. Total amount of liquid detergent: 35 g in each case; washing machine model: Miele Novotronic W135; standard wash (cold): 20° C.

Participating in the comparative tests were 14 testers (non-experts from a perfume standpoint), who assessed the fragrance, based in each case on the odor of the product as such, and also of the odor of the laundry in both the damp and dry states. By damp stage is meant that, after spinning, the damp laundry was removed from the drum and its fragrance was assessed. The laundry was then dried on the line. The fragrance of the dry laundry was assessed after two days, the individual items of dry laundry being stored carefully separated from one another in open plastic bags. The specimens were assessed in a blind comparison—that is, the testers did not know that the conditioners contained different perfumes.

Result.

With Regard to the Pure Liquid Laundry Detergents.

Twelve testers expressed the opinion that, in terms of odor, the pure liquid detergents a) and b) were indistinguishable. Two testers announced an ability to distinguish them. Eleven testers were of the view that detergents c) were different from compositions a) and b). One tester was unable to find any difference and declared all of the compositions to be of equal odor.

With Regard to the Damp Laundry.

Thirteen testers expressed the opinion that, in terms of odor, the damp laundry washed with detergents a) and b) were indistinguishable. Of these thirteen, however, nine testers stated that although the laundry washed with a) smelled the same, the fragrance sensation was nevertheless more intense in the case of a). Nine testers were of the view that the laundry washed with liquid detergent c) was different in terms of odor from a) and b). The laundry washed with a) and b), moreover, was said to have a fresher and more intense smell. Five testers were unable to ascertain any difference and declared all of the compositions to smell the same. Of these five, two declared that c), although it smelled the same, had a less intense smell.

With Regard to the Dry Laundry.

All of the testers expressed the opinion that, in terms of odor, the dry laundry washed with liquid detergents a) and b) were indistinguishable. Of these fourteen, however, nine testers stated that, although the laundry washed with a) smelled the same, the fragrance sensation was nevertheless significantly weaker in the case of b). Eight testers were of the view that the laundry washed with detergent c) was different in terms of odor from a) and b). The laundry washed with a) and b), moreover, was said to have a fresher smell. The laundry washed with c), moreover, was said to have a much weaker smell. Six testers were unable to ascertain any difference and declared all of the compositions to smell the same. Of these six, two declared that c), although it smelled the same, had a less intense smell.

Examples 9 to 11

Three solid laundry detergents were produced, with the formula given below. They were identical except for the perfume component. Solid laundry detergent a) contained 40% by weight of FP1, detergent b) 40% by weight of geranonitrile, and detergent c) 40% by weight of 3,7-dimethyloct-6-enenitrile, based in each case on the total perfume present.

Solid Laundry Detergent. Examples 9 to 11.

| Raw material | Amount in % by weight |
|---|---|
| Alkylbenzenesulfonate (sodium salt) | 12 |
| Carboxymethylcellulose | 1 |
| Enzymes | 1 |
| Nonionic surfactant | 3 |
| (1-hydroxyethylidene)bisphosphonate | 1 |
| Sodium carbonate | 25 |
| Sodium percarbonate | 12 |
| Sodium sulfate | 27 |
| Polyacrylate | 3 |
| Defoamer | 2 |
| N,N,N',N'-tetraacetylethylenediamine | 3 |
| Water | 3 |
| Perfume | 1 |
| Sodium silicate | ad 100 |
| Total | 100 |

Sodium silicate: amorphous sodium silicate with $Na_2O:SiO_2$ = 2.4

Polyacrylate: Norasol LMW 45N ®; polyacrylic acid, sodium salt; M = 4500 g/mol; commercial product from NorsoHaas These solid laundry detergents were then used to treat cotton laundry (twelve white hand towels) in a washing machine. Total amount of solid detergent: 35 g in each case; washing machine model: Miele Novotronic W135; standard wash (cold): 20° C.

Participating in the comparative tests were twelve testers (non-experts from a perfume standpoint), who assessed the fragrance, based in each case on the odor of the product as such, and also on the odor of the laundry in both the damp and dry states. By damp state is meant that, after spinning, the damp laundry was removed from the drum and its fragrance was assessed. The laundry was then dried on the line. The fragrance of the dry laundry was assessed after two days, the individual items of dry laundry being stored carefully separated from one another in open plastic bags. The specimens were assessed in a blind comparison—that is, the testers did not know that the conditioners contained different perfumes.

Result.

With Regard to the Pure Solid Detergent.

Ten testers expressed the opinion that, in terms of odor, the pure solid detergents a) and b) were indistinguishable. Two testers announced an ability to distinguish them. Nine testers were of the view that composition c) was different from compositions a) and b). Three testers were unable to find any difference and declared all of the compositions to be of equal odor.

With Regard to the Damp Laundry.

Twelve testers expressed the opinion that, in terms of odor, the loads of damp laundry washed with solid detergents a) and b) were indistinguishable. Of these twelve, however, nine testers stated that, although the laundry washed with a) smelled the same, the fragrance sensation was nevertheless more intense in the case of a). Eight testers were of the view that the laundry washed with composition c) was different in terms of odor from a) and b). Four testers were unable to ascertain any difference and declared all of the compositions to smell the same.

With Regard to the Dry Laundry.

All of the testers expressed the opinion that, in terms of odor, the loads of dry laundry washed with solid detergents a) and b) were indistinguishable. Of these twelve, however, nine testers stated that, although the laundry washed with a) smelled the same, the fragrance sensation was nevertheless significantly weaker in the case of b). Six testers were of the view that the laundry washed with composition c) was different in terms of odor from a) and b). The laundry washed with a) and b), moreover, was said to have a fresher smell. The laundry washed with c), moreover, was said to have a much weaker smell. Six testers were unable to ascertain any difference and declared all of the compositions to smell the same. Of these six, five declared regarding c), that although it smelled the same, had a less intense smell.

Examples 12 to 14

Three gel laundry detergents were produced, with the formula given below. They were identical except for the perfume component. Gel laundry detergent a) contained 40% by weight of FP1, detergent b) 40% by weight of geranonitrile, and detergent c) 40% by weight of 3,7-dimethyloct-6-enenitrile, based in each case on the total perfume present.

Gel Laundry Detergent Examples 12 to 14

| Raw material | Amount in % by weight |
|---|---|
| Alkylpolyglucoside | 2.00 |
| C12-14 soap, Na | 8.80 |
| C16-18 soap, Na | 6.80 |
| NaOH 50% | 3.00 |
| Citric acid × $1H_2O$ | 1.00 |
| Glycerol 99.5% | 7.50 |
| Ethanol | 1.00 |
| Silicone defoamer | 0.30 |
| Boric acid | 1.00 |
| 1-Hydroxyethylenediphosphonic acid | 0.50 |
| Vinylimidazole-vinylpyrrolidone copolymer | 1.67 |
| Perfume | 1.3 |
| Water | ad 100 |

Examples 15 to 17

Three ironing fluids were produced, with the formula given below. They were identical except for the perfume component. Ironing fluid a) contained 40% by weight of FP1, fluid b) 40% by weight of geranonitrile, and fluid c) 40% by weight of 3,7-dimethyloct-6-enenitrile, based in each case on the total perfume present.

Ironing Fluid Comparative Example 11

| Raw material | Amount in % by weight |
|---|---|
| Ethanol | 2 |
| Hydrogen peroxide | 0.01 |
| Perfume | 0.3 |
| Water with 5° dH [German hardness] | ad 100% by weight |

The invention claimed is:

1. A fragrance preparation consisting of 3,7-dimethyloct-6-enenitrile and at least one component selected from the group consisting of:

a) undecanal isomer mixture, b) 2-butyl-4,6-dimethyldihydropyran, c) 2-benzyl-2-methyl-3-butenenitrile, d) 2,4-dimethyl-4-phenyltetrahydrofuran, e) ethylmethoxynorbornane isomer mixture, f) cis-, trans-3-methyl-5-phenyl-2-pentenenitrile, and/or g) 9-decen-1-ol, wherein the fragrance preparation is an equivalent replacement for geranonitrile with respect to odor profile, yet does not have the toxicological effect of geranonitrile.

2. The fragrance preparation of claim 1, wherein i) the weight ratio of 3,7-dimethyloct-6-enenitrile to undecanal isomer mixture is from 300:1 to 1:5, and/or ii) the weight ratio of 3,7-dimethyloct-6-enenitrile to 2-butyl-4,6-dimethyldihydropyran is from 200:1 to 1:9, and/or iii) the weight ratio of 3,7-dimethyloct-6-enenitrile to 2-benzyl-2-methyl-3-butenenitrile is from 200:1 to 1:13, and/or iv) the weight ratio of 3,7-dimethyloct-6-enenitrile to 2,4-dimethyl-4-phenyltetrahydrofuran is from 300:1 to 1:13, and/or v) the weight ratio of 3,7-dimethyloct-6-enenitrile to ethyl methoxynorbornane isomer mixture is from 400:1 to 1:2, and/or vi) the weight ratio of 3,7-dimethyloct-6-enenitrile to cis-, trans-3-methyl-5-phenyl-2-pentenenitrile is from 200:1 to 1:5, and/or vii) the weight ratio of 3,7-dimethyloct-6-enenitrile to 9-decen-1-ol is from 400:1 to 1:5.

3. A composition comprising the fragrance preparation of claim 1.

4. A composition comprising the fragrance preparation of claim 2.

5. The composition of claim 3, wherein the weight fraction of the fragrance preparation is between $\geqq 10^{-6}$% by weight and $\leqq 50$% by weight based on the total weight of the composition.

6. The composition of claim 3 further comprising at least one additional fragrance.

7. The composition of claim 3, wherein the composition comprises a supported fragrance.

8. The composition of claim 3, wherein the composition comprises at least one active laundering, care and/or cleaning component.

9. A method of producing a citrus odor in a composition comprising adding to said composition a citrus odor-producing effective amount of a fragrance preparation of claim 1.

10. The composition of claim 5, wherein the weight fraction of the fragrance preparation is between $\geqq 0.03$% by weight and $\leqq 5$% by weight, based on the total weight of the composition.

* * * * *